United States Patent
Ikeda et al.

(10) Patent No.: US 11,045,073 B2
(45) Date of Patent: Jun. 29, 2021

(54) FLEXIBLE TUBE INSERTION APPARATUS

(71) Applicant: OLYMPUS CORPORATION, Tokyo (JP)

(72) Inventors: Yuichi Ikeda, Tama (JP); Shuji Nakamura, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 436 days.

(21) Appl. No.: 16/016,852

(22) Filed: Jun. 25, 2018

(65) Prior Publication Data

US 2018/0303319 A1    Oct. 25, 2018

Related U.S. Application Data

(63) Continuation of application No. PCT/JP2015/086391, filed on Dec. 25, 2015.

(51) Int. Cl.
*A61B 1/00* (2006.01)
*A61B 1/005* (2006.01)
(Continued)

(52) U.S. Cl.
CPC ...... *A61B 1/00078* (2013.01); *A61B 1/00006* (2013.01); *A61B 1/0051* (2013.01);
(Continued)

(58) Field of Classification Search
CPC combination set(s) only.
See application file for complete search history.

(56) References Cited

U.S. PATENT DOCUMENTS 5,269,289 A * 12/1993 Takehana ........... A61B 1/00147
348/E5.034
5,307,803 A * 5/1994 Matsuura ............. A61B 1/0051
138/118
(Continued)

FOREIGN PATENT DOCUMENTS

EP    1 857 038 A2    11/2007
JP    H04-067829 A    3/1992
(Continued)

OTHER PUBLICATIONS

Japanese Office Action dated Jul. 2, 2019 in Japanese Patent Application No. 2017-557657.
(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

A flexible tube insertion apparatus includes an insertion section, a stiffness variable unit that changes a bending stiffness of the insertion section and a detection unit that detects an advance that is a movement toward a distal end of the insertion section and a retreat that is a movement toward a proximal end of the insertion section. A controller controls the stiffness variable unit to change the bending stiffness of the insertion section to a first bending stiffness when the detection unit has detected the advance of the insertion section, and that controls the stiffness variable unit to change the bending stiffness of the insertion section to a second bending stiffness higher than the first bending when the detection unit has detected the retreat of the insertion section.

4 Claims, 16 Drawing Sheets

(51) Int. Cl.
*A61B 5/06* (2006.01)
*A61M 25/00* (2006.01)
*A61M 25/01* (2006.01)
*A61B 1/05* (2006.01)

(52) U.S. Cl.
CPC ................ *A61B 5/06* (2013.01); *A61B 1/05* (2013.01); *A61M 25/0102* (2013.01); *A61M 2025/0063* (2013.01)

(56) References Cited

U.S. PATENT DOCUMENTS

| | | | | |
|---|---|---|---|---|
| 5,885,208 A | * | 3/1999 | Moriyama | A61B 1/00078 600/144 |
| 6,432,041 B1 | | 8/2002 | Taniguchi et al. | |
| 2002/0161281 A1 | * | 10/2002 | Jaffe | A61B 5/065 600/114 |
| 2006/0089531 A1 | * | 4/2006 | Tartaglia | A61B 1/00154 600/114 |
| 2007/0043261 A1 | * | 2/2007 | Watanabe | A61B 1/00078 600/144 |
| 2007/0149852 A1 | * | 6/2007 | Noguchi | A61B 1/0051 600/144 |
| 2007/0249932 A1 | * | 10/2007 | Shahinian | A61B 1/00193 600/421 |
| 2007/0270649 A1 | * | 11/2007 | Long | A61B 1/0053 600/144 |
| 2008/0221592 A1 | | 9/2008 | Kawai | |
| 2009/0018390 A1 | * | 1/2009 | Honda | A61B 18/1492 600/106 |
| 2009/0281384 A1 | * | 11/2009 | Tsumaru | A61B 1/0016 600/114 |
| 2011/0230712 A1 | * | 9/2011 | Matsuura | A61B 1/0646 600/106 |
| 2014/0190305 A1 | * | 7/2014 | Okamoto | G02B 23/2476 74/490.04 |
| 2017/0281288 A1 | * | 10/2017 | Au | A61B 1/00078 |

FOREIGN PATENT DOCUMENTS

| | | | | |
|---|---|---|---|---|
| JP | H06-304127 A | | 11/1994 | |
| JP | H10-179509 A | | 7/1998 | |
| JP | 2003-000533 A | | 1/2003 | |
| JP | 3772157 B2 | * | 5/2006 | ......... A61B 1/00078 |
| JP | 4589560 B2 | * | 12/2010 | ......... A61B 1/00078 |
| JP | 4624711 B2 | * | 2/2011 | ......... A61B 1/00078 |
| JP | 4772208 B2 | * | 9/2011 | ......... A61B 1/00078 |
| JP | 5326049 B2 | * | 10/2013 | ......... A61B 1/00073 |
| JP | 2013-248346 A | | 12/2013 | |
| JP | 5371185 B2 | * | 12/2013 | ........... A61B 1/0016 |
| JP | 5371185 B2 | | 12/2013 | |
| WO | WO-2005102144 A1 | * | 11/2005 | ......... A61B 1/00071 |
| WO | WO-2011055613 A1 | * | 5/2011 | ......... A61B 1/00147 |
| WO | WO-2012132638 A1 | * | 10/2012 | .............. A61B 6/02 |
| WO | WO-2013172089 A1 | * | 11/2013 | ......... G02B 23/2476 |

OTHER PUBLICATIONS

English translation of International Preliminary Report on Patentability dated Jul. 5, 2018 together with the Written Opinion received in related International Application No. PCT/JP2015/086391.
International Search Report dated Mar. 15, 2016 issued in PCT/JP2015/086391.
English Abstract of JP 2008-099743 dated May 1, 2008.
Extended Supplementary European Search Report dated Jul. 11, 2019 received in European Patent Application No. 15 91 1420.6.

* cited by examiner

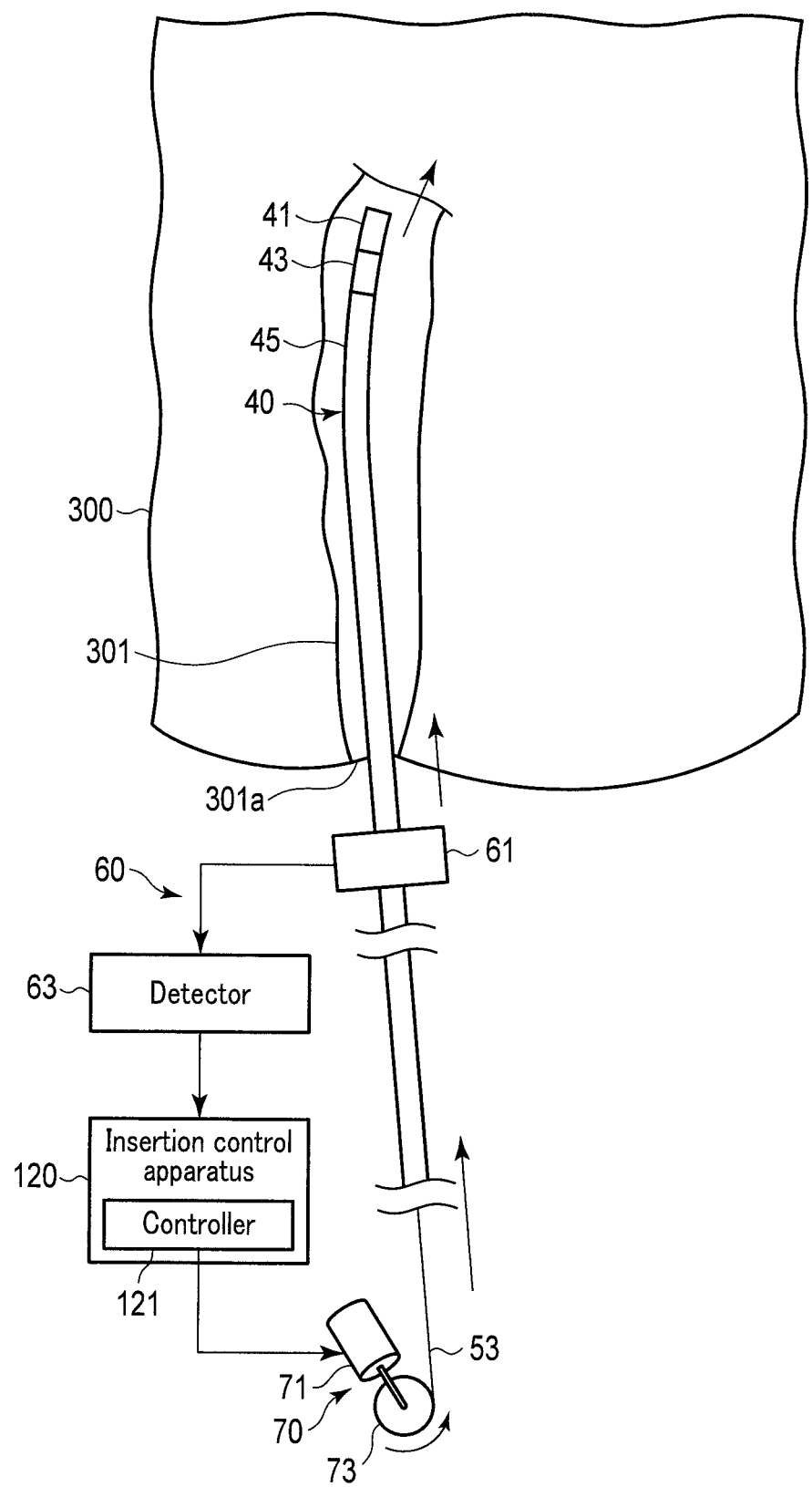
F I G. 2A

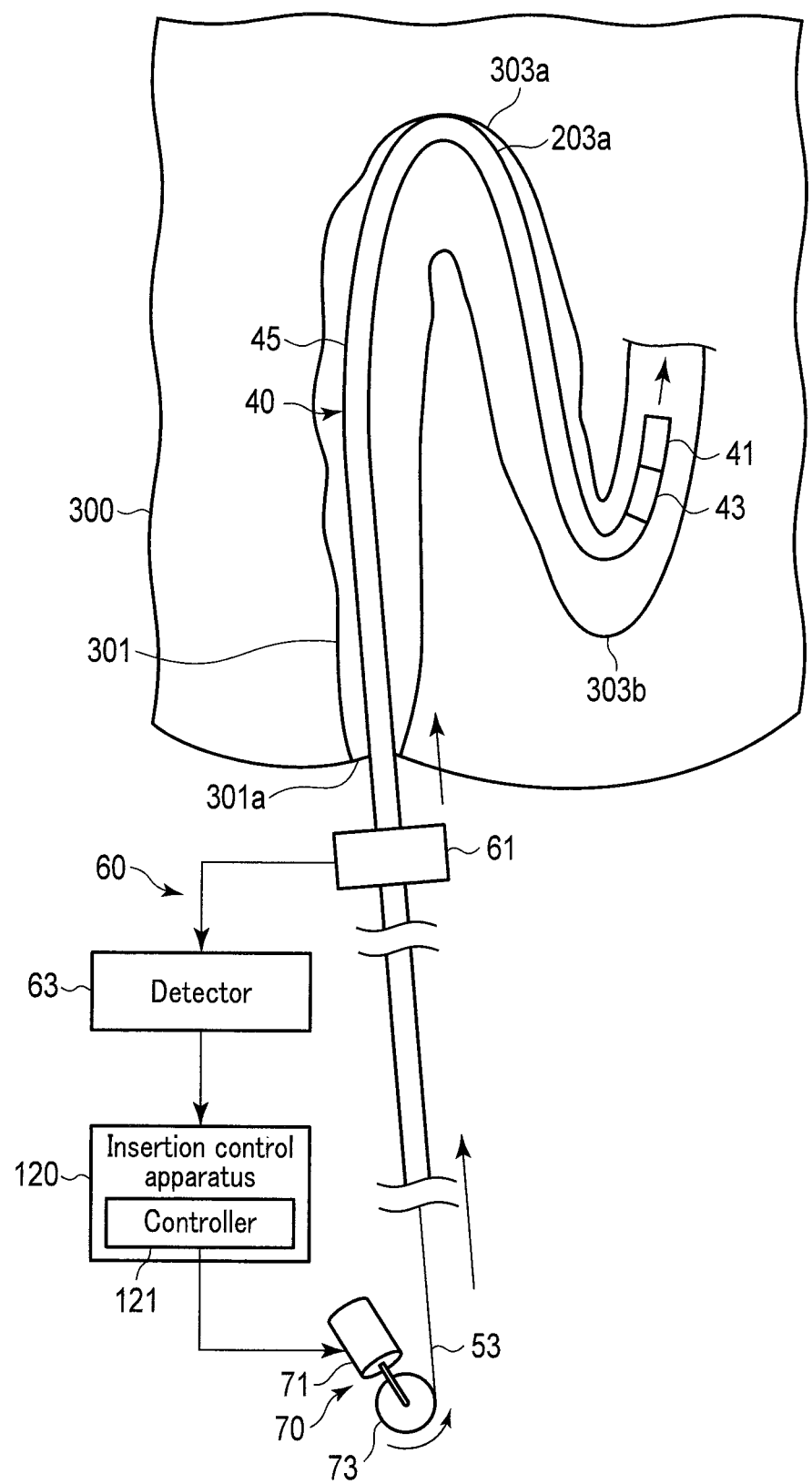
F I G. 2B

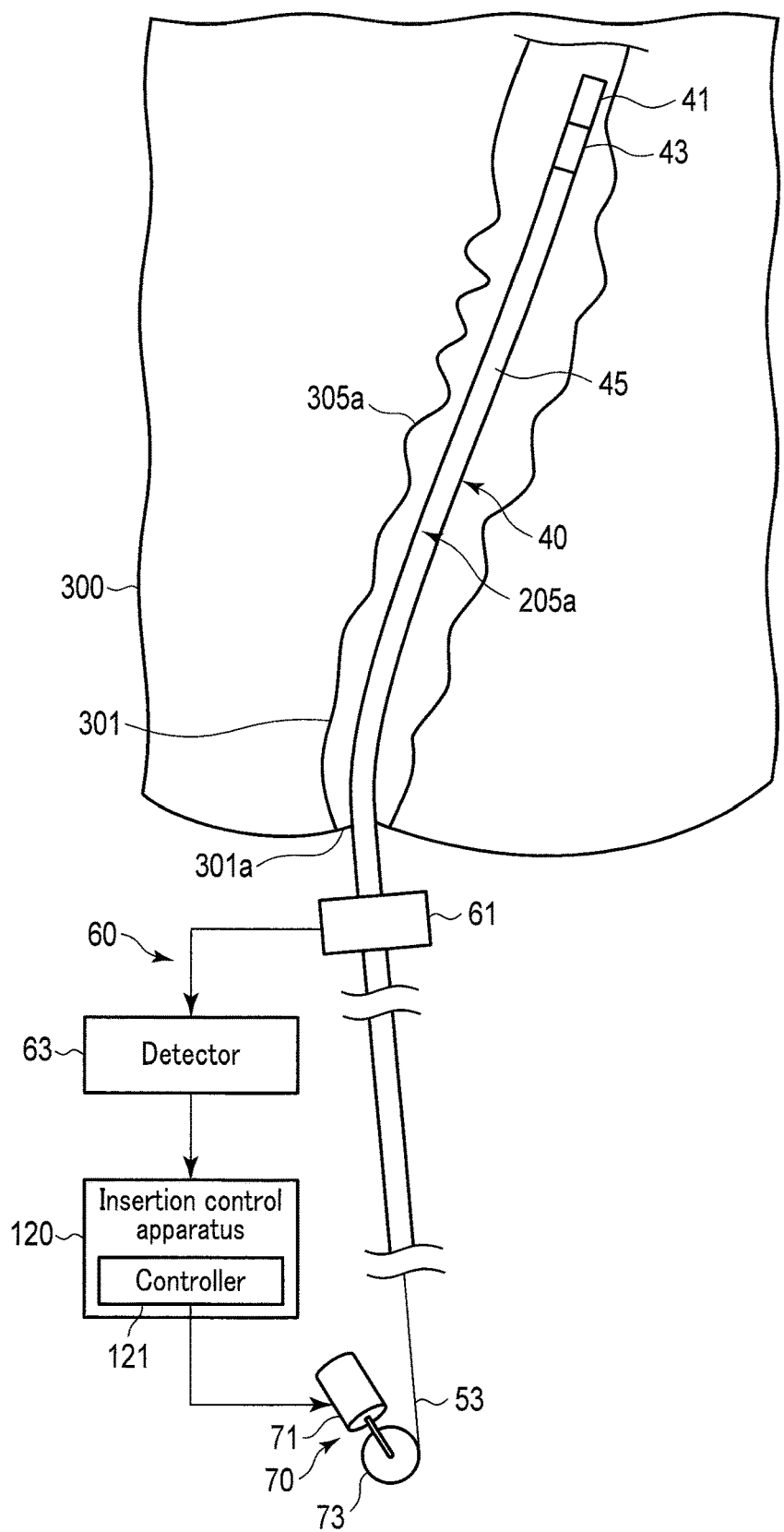
F I G. 2E

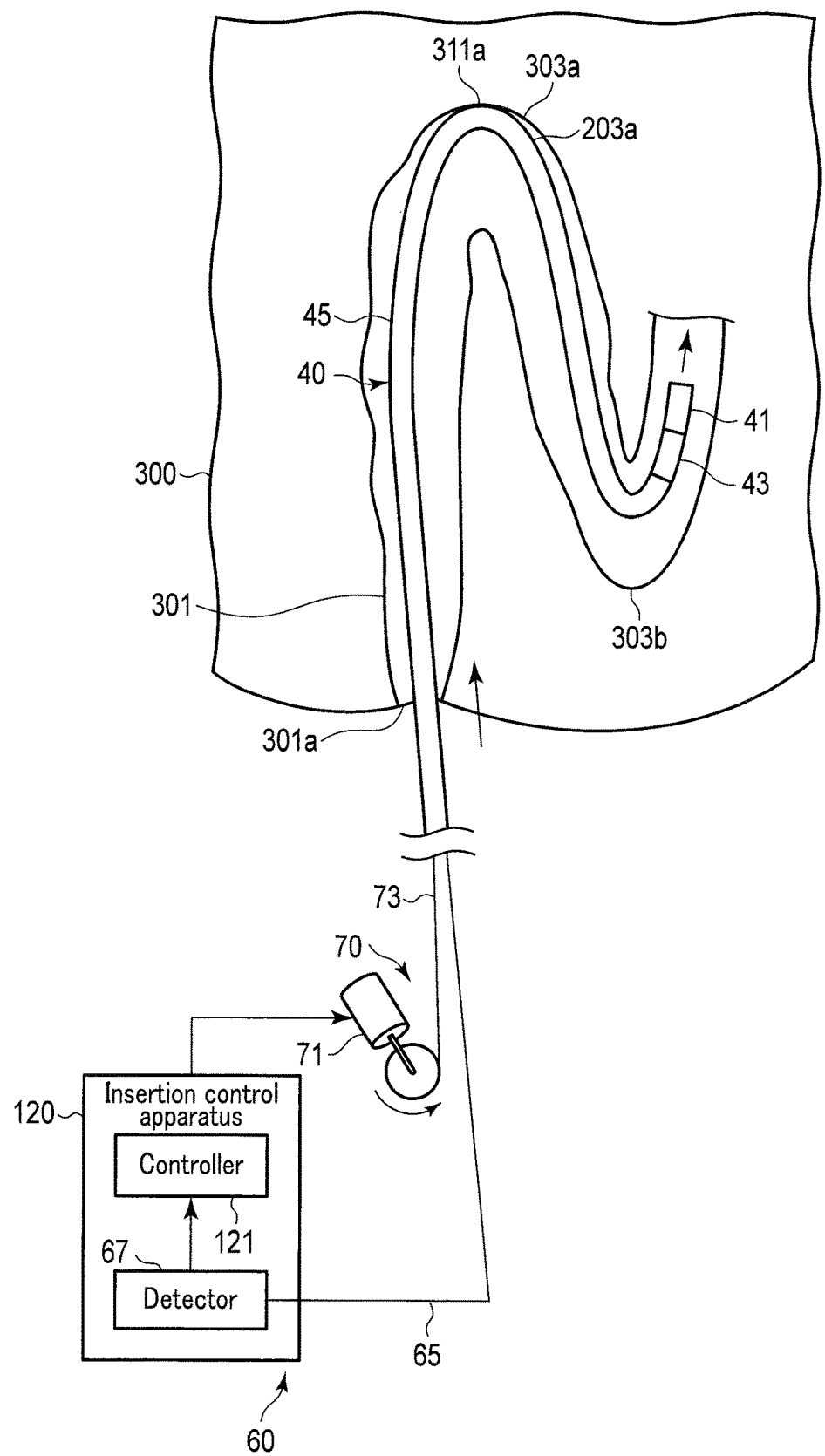
F I G. 4A

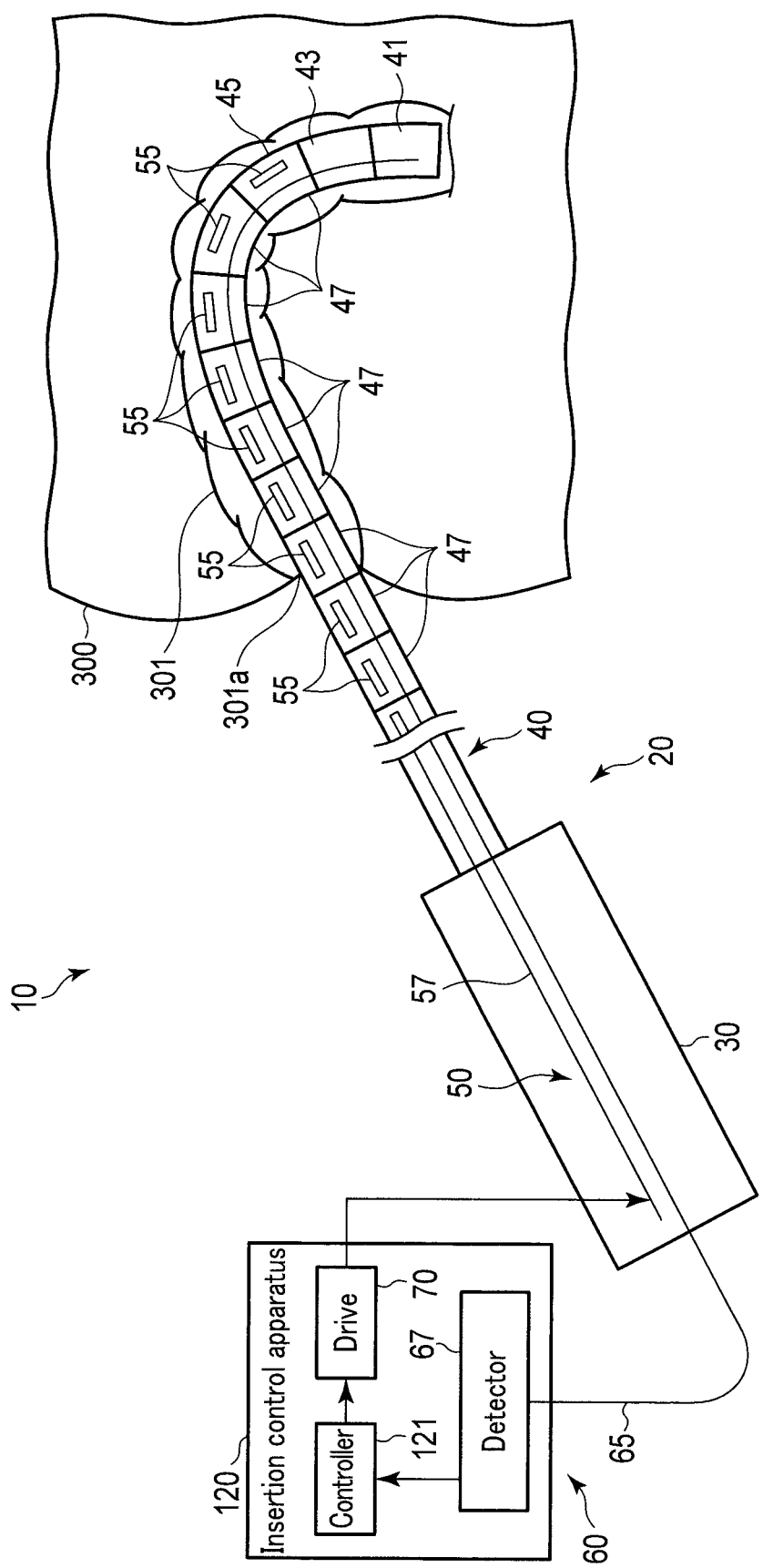
F I G. 5

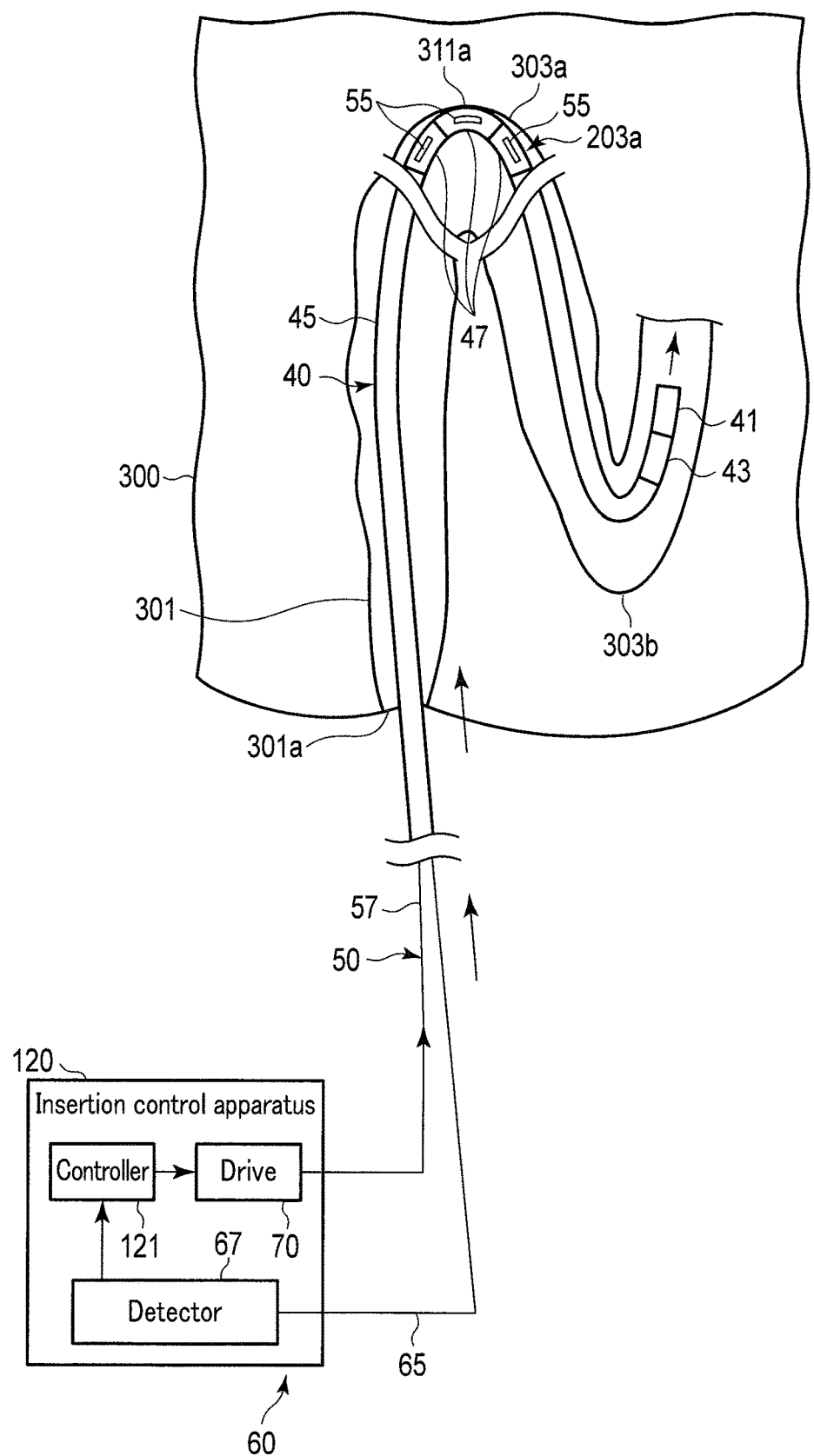
F I G. 6A

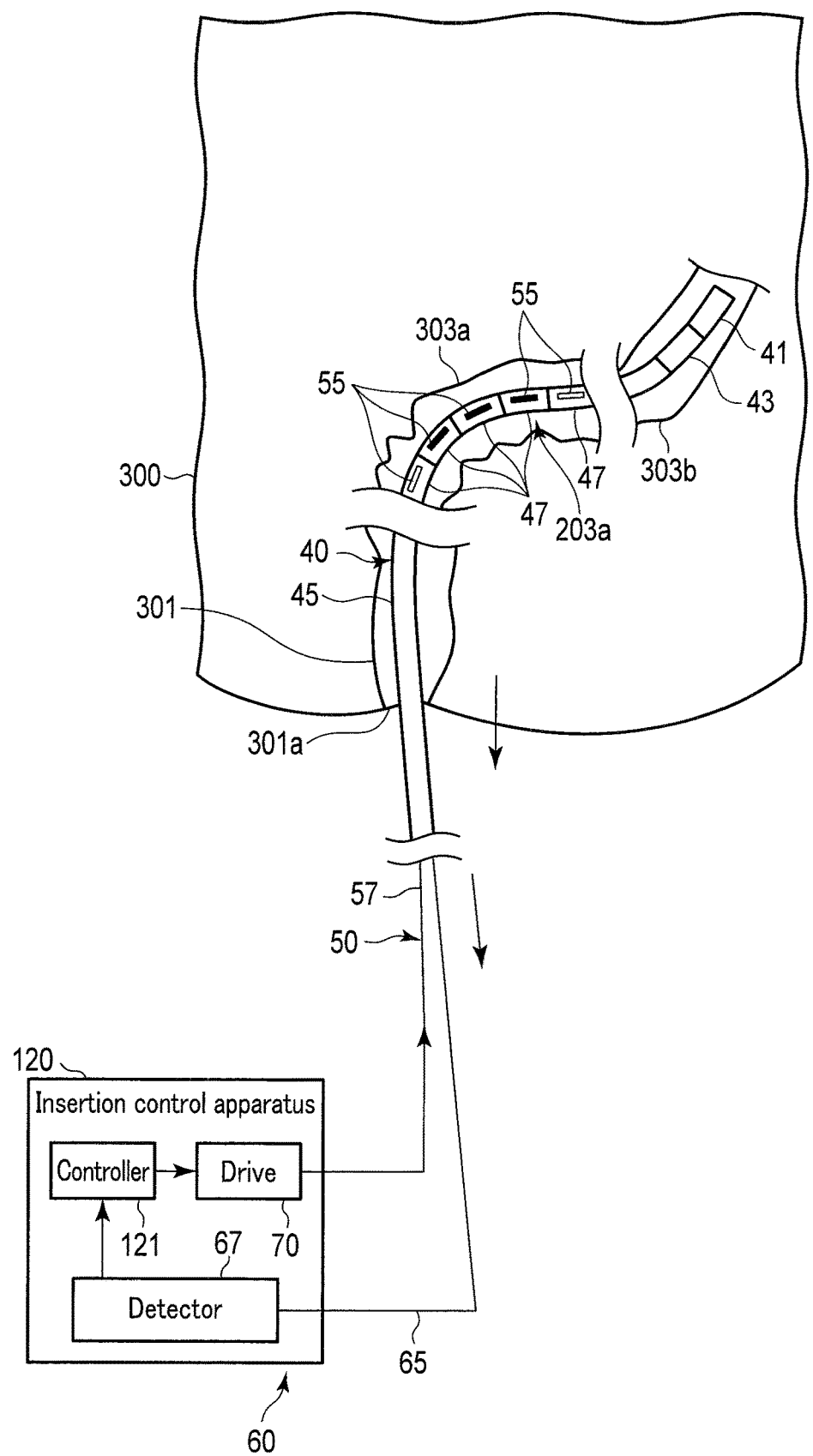
F I G. 6C

FLEXIBLE TUBE INSERTION APPARATUS

CROSS-REFERENCE TO RELATED APPLICATIONS

This application is a Continuation Application of PCT Application No. PCT/JP2015/086391, filed Dec. 25, 2015, the entire contents of which are incorporated herein by references.

BACKGROUND OF THE INVENTION

1. Field of the Invention

The present invention relates to a flexible tube insertion apparatus.

2. Description of the Related Art

A flexible tube insertion apparatus, which is an endoscope apparatus, comprises an endoscope. An insertion section of the endoscope is inserted into the inside of a tube portion, and is further inserted toward a deep portion of the tube portion from the inside of the tube portion. The deep portion refers to a position ahead of the current position as viewed in the insertion direction of the insertion section. The tube portion refers to a flexible and bended tube portion that is movable in accordance with, for example, an insertion operation of the insertion section. An example of such a tube portion is the large intestine. Hereinafter, an explanation will be given by taking the large intestine as an example. To allow the insertion section to be easily inserted toward the deep portion, a procedure for substantially straightening the large intestine is known that changes the large intestine to a substantially straight state, by a combination of a push operation, a pull-back operation, and a twist operation for the insertion section. By changing a bent portion of the large intestine to a substantially straight state, the operation force from the hand side toward the insertion section is easily transmitted to a distal end side of the insertion section, allowing the distal end of the insertion section to be easily advanced toward the deep portion.

However, when the push operation is performed excessively, an overextension may occur in the bent portion by the push operation. Such an overextension causes distress to the patient. If a pull-back operation is performed early to avoid the overextension, the insertion section will be withdrawn from the large intestine before the large intestine is changed to a substantially straight state. Accordingly, the operator cannot perform the procedure for substantially straightening the large intestine, and the large intestine does not change to a substantially straight state.

Thus, it is difficult to perform the operation procedure for changing the large intestine to a substantially straight state by a complex operation that is a combination of a push operation, a pull-back operation, and a twist operation at the hand side of the insertion section. Such an operation procedure has a problem in that it requires much training to acquire, and that the operator is forced to bear the burden.

An endoscope system disclosed in Jpn. Pat. Appln. KOKAI Publication No. 2013-248346, for example, includes a passively-bendable portion and an insertion section. The passively-bendable portion is passively bent by an external force from a bent portion at the time of a push operation of the insertion section. The insertion section includes the passively-bendable portion. The insertion section is inserted toward a deep portion along the bent portion by the passively-bendable portion. To change the large intestine to a substantially straight state, an overtube that covers the passively-bendable portion is used. The overtube prevents the passively-bendable portion from being bent by an external force, increases the bending stiffness of the insertion section, and changes the bent portion to a substantially straight state.

An intraluminal insertion apparatus disclosed in Jpn. Pat. Appln. KOKAI Publication No. H4-67829, for example, includes an insertion amount detection means for detecting an amount of insertion of the insertion section. The intraluminal insertion apparatus controls advances and retreats and rotations of the insertion section in accordance with the amount of insertion.

Jpn. Pat. Appln. KOKAI Publication No. 2003-533 and Japanese Patent No. 5371185, for example, discloses a variable stiffness mechanism that makes the large intestine substantially straight by increasing the bending stiffness of the insertion section.

BRIEF SUMMARY OF THE INVENTION

According to an aspect of the present invention, a flexible tube insertion apparatus comprising an insertion section including a distal end and a proximal end and configured to be inserted into a subject from the distal end, a stiffness variable unit that is provided in the insertion section and that changes a bending stiffness of the insertion section, an advance and retreat detection unit that detects an advance that is a movement toward a direction of the distal end of the insertion section and a retreat that is a movement toward a direction of the proximal end of the insertion section, and a controller that controls the stiffness variable unit to change the bending stiffness of the insertion section to a first bending stiffness when the advance and retreat detection unit has detected the advance of the insertion section, and that controls the stiffness variable unit to change the bending stiffness of the insertion section to a second bending stiffness higher than the first bending when the advance and retreat detection unit has detected the retreat of the insertion section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2A is a diagram showing a state in which an insertion section of the flexible tube insertion apparatus shown in FIG. 1 is advancing toward a first bent portion.

FIG. 2B is a diagram showing a state in which the insertion section shown in FIG. 2A is advancing toward a deep portion through the first bent portion.

FIG. 2E is a diagram showing a state in which the insertion section shown in FIG. 2D is changed to a substantially straight state by the retreat of the insertion section.

FIG. 4A is a diagram showing a state in which an insertion section of the flexible tube insertion apparatus shown in FIG. 3 is advancing toward a deep portion through a first bent portion.

FIG. 5 is a schematic diagram of a flexible tube insertion apparatus according to a second variant of the first embodiment.

FIG. 6A is a diagram showing a state in which an insertion section of the flexible tube insertion apparatus shown in FIG. 5 is advancing toward a deep portion through a first bent portion.

FIG. 6C is a diagram showing a state in which the insertion section shown in FIG. 6B is changed to a substantially straight state by the retreat of the insertion section.

DETAILED DESCRIPTION

Hereinafter, embodiments of the present invention will be explained in detail with reference to the accompanying drawings. In some of the drawings, illustration of some members is omitted for clarification of the illustration. A deep portion refers to a position ahead of the current position as viewed in an insertion direction of an insertion section 40. In the present embodiment, in a push operation and a pull-back operation of the insertion section 40, the operator grips a given position of the insertion section 40 that is exposed to the outside from a tube portion 301, in a state in which a distal end portion of the insertion section 40 is inserted into the inside of the tube portion 301 from an entrance 301a of the tube portion 301, for example. The push operation refers to pushing the insertion section 40 with a pushing force exerted on the insertion section 40 by the operator from the gripped part. Thereby, the distal end portion of the insertion section 40 is pushed into a deep portion that is present ahead of the entrance 301a, and advances toward the deep portion. The pull-back operation refers to pulling back the insertion section 40 with a pull-back force exerted on the insertion section 40 by the operator from the gripped part. Thereby, the distal end portion of the insertion section 40 is pulled back to the hand side from the deep portion, and retreats toward the entrance 301a.

First Embodiment

[Configuration]

An explanation will now be given of the first embodiment, with reference to the accompanying drawings.

[Flexible Tube Insertion Apparatus (hereinafter Referred to as an Insertion Apparatus 10)]

Figure 1:
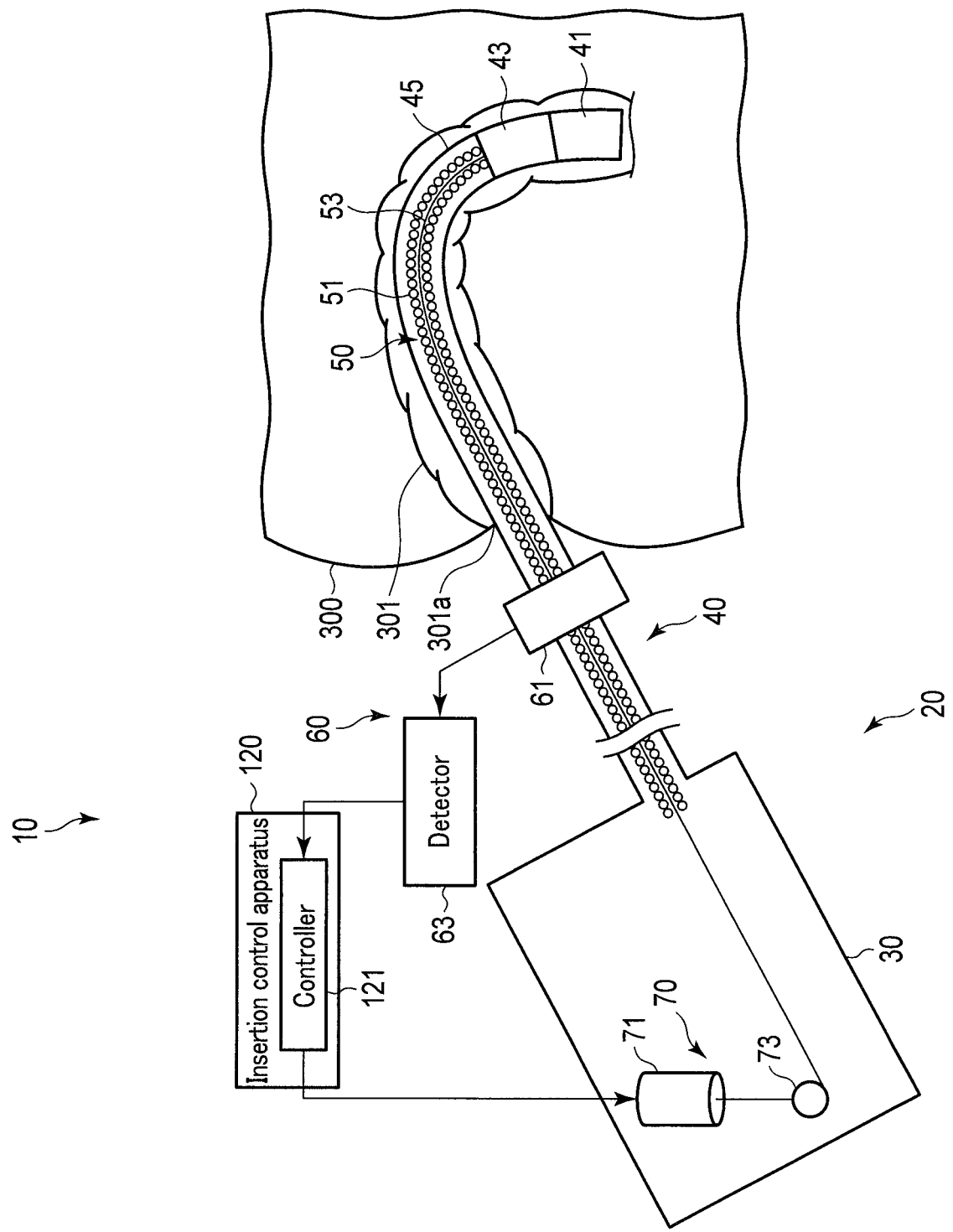
FIG. 1 is a schematic diagram of a flexible tube insertion apparatus according to a first embodiment of the present invention.

An insertion apparatus 10, which is an endoscope apparatus as shown in FIG. 1, is installed in, for example, an operation room or an examination room. The insertion apparatus 10 includes an endoscope 20 for medical use and an insertion control apparatus 120 connected to the endoscope 20. The insertion apparatus 10 includes a light source apparatus (not shown in the drawings) connected to the endoscope 20, an image control apparatus (not shown in the drawings) connected to the endoscope 20, a display apparatus (not shown in the drawings) connected to the image control apparatus, and an input apparatus (not shown in the drawings) connected to the image control apparatus.

The endoscope 20 is, for example, an example of an insertion apparatus that is inserted into a subject 300 including the tube portion 301, which is, for example, the large intestine. The endoscope 20 images the inside of the tube portion 301 using an image sensor of an imaging unit (not shown in the drawings). The image sensor includes, for example, a CCD.

The light source apparatus (not shown in the drawings) emits light to allow the image sensor to perform imaging. The light is guided to an illumination portion (not shown in the drawings) of the illumination unit by a light guide member (not shown in the drawings) of the illumination unit provided inside the endoscope 20. The light is emitted from the illumination portion toward the outside as illumination light. An image taken by the image sensor is output to an image control apparatus (not shown in the drawings) from the image sensor via a signal line of the imaging unit provided inside the endoscope 20.

The image control apparatus (not shown in the drawings) performs signal processing in such a manner that the image taken by the image sensor is displayed on a display apparatus (not shown in the drawings). The image control apparatus includes, for example, a CPU. The display apparatus includes, for example, a monitor.

The insertion control apparatus 120 controls the bending stiffness of the insertion section 40 provided in the endoscope 20; however, the details will be described later.

The endoscope 20 will be explained as a medical flexible endoscope as an example, but is not limited thereto. For example, the endoscope 20 may be a flexible endoscope for industrial use. Instead of the endoscope 20, a catheter, a treatment instrument, etc., may be used. The endoscope 20, the catheter, the treatment instrument, etc., are only required to include a flexible insertion section 40 to be inserted into the subject 300. The subject 300 is not limited to, for example, a human, and may be an animal or any other structural object. The endoscope 20 may be a front-viewing endoscope 20, or a side-viewing endoscope 20.

The endoscope 20 includes an operation section 30 gripped by the operator and the insertion section 40 to be inserted into the subject 300.

The operation section 30 is continuous with a proximal end portion of the insertion section 40. The operation section 30 includes a bending operation portion (not shown in the drawings) used to operate a bendable portion 43, which will be described later, and a switch portion (not shown in the drawings) used to operate a plurality of units such as the imaging unit. The operation section 30 further includes a universal cord (not shown in the drawings), and is connected, via the universal cord, to the light source apparatus (not shown in the drawings), the image control apparatus (not shown in the drawings), and the insertion control apparatus 120.

The insertion section 40 is tubular, elongated, and flexible. The insertion section 40 advances and retreats inside the tube portion 301 with respect to the tube portion 301. The insertion section 40 is bendable along the shape inside of the tube portion 301. The insertion section 40 includes a distal rigid portion 41, the bendable portion 43, and a flexible tube 45 in this order from the distal end portion of the insertion section 40 toward the proximal end portion of the insertion section 40. A proximal end portion of the distal rigid portion 41 is coupled to a distal end portion of the bendable portion 43, a proximal end portion of the bendable portion 43 is coupled to a distal end portion of the flexible tube 45, and a proximal end portion of the flexible tube 45 is coupled to the operation section 30. The image sensor and the illumination portion are provided inside the distal rigid portion 41.

As shown in FIG. 1, the insertion apparatus 10 includes a stiffness variable unit 50 that is arranged in the insertion section 40 and is variable in stiffness. More specifically, the stiffness variable unit 50 is incorporated into the insertion section 40. The stiffness variable unit 50 needs to be incorporated at least into the flexible tube 45. A distal end portion of the stiffness variable unit 50 is arranged at, for example, the distal end portion of the flexible tube 45. A proximal end portion of the stiffness variable unit 50 is arranged inside, for example, the operation section 30.

The stiffness variable unit 50 includes, for example, a coiled sheath member 51 incorporated into the insertion section 40, and a wire member 53 that is inserted through an inside of the sheath member 51. The sheath member 51 includes a distal end portion arranged at the distal end portion of the flexible tube 45, and a proximal end portion fixed to the inside of the operation section 30. The sheath member 51 can be extended or contracted as viewed in an axis direction of the sheath member 51. The sheath member 51 has an elastic force that allows the sheath to, after being contracted, return to its initial length before the contraction. The reference state of the sheath member 51 is the extended state. The wire member 53 includes a distal end portion fixed to the distal end portion of the sheath member 51, and a proximal end portion arranged inside the operation section 30. The proximal end portion of the wire member 53 is connected to a drive 70, which will be described later.

The wire member 53 contracts the sheath member 51 in the axis direction of the sheath member 51 by pulling the drive 70. More specifically, the wire member 53 is pulled toward the proximal end portion of the insertion section 40 by the drive 70. The wire member 53 pulls the sheath member 51 toward the proximal end portion of the insertion section 40 by being pulled by the drive 70, and the sheath member 51 is contracted toward the proximal end portion of the sheath member 51 by being pulled by the wire member 53. Accordingly, the sheath member 51 is increased in stiffness, the bending stiffness of the insertion section 40 is uniformly increased in the entire part in which the sheath member 51 is arranged, and the insertion section 40 is changed from a bent state to a substantially straight state. That is, the insertion section 40 comes into a substantially straight state.

Conversely, when the pull of the wire member 53 is released by the drive 70, the contraction of the sheath member 51 is released. Thereby, the sheath member 51 is extended to return to its original length by an elastic force of the sheath member 51. Accordingly, the sheath member 51 is decreased in stiffness, the bending stiffness of the insertion section 40 is uniformly decreased in the entire part in which the sheath member 51 is arranged, the bending stiffness of the insertion section 40 returns to the initial value, and the insertion section 40 is changed from a substantially straight state to a bent state. That is, the insertion section 40 is in a state of being passively bendable by an external force, etc. The external force refers to, for example, a force exerted on the insertion section 40 from a given angle with respect to the central axis of the insertion section 40.

Thus, the stiffness of the sheath member 51 changes according to the amount of pull by the wire member 53, and the bending stiffness of the insertion section 40 incorporating the sheath member 51 changes in accordance with the stiffness of the sheath member 51. At this time, the stiffness variable unit 50, for example, uniformly varies (changes) the bending stiffness of the entire insertion section 40. The stiffness variable unit 50 controls the bending stiffness of the insertion section 40 to be a bending stiffness that makes the insertion section 40 to be substantially straight, in accordance with the stiffness of the sheath member 51.

The amount of pull of the wire member 53 by the drive 70 is restricted to a desired amount by a restricting mechanism (not shown in the drawings). The restricting mechanism works on, for example, one of the sheath member 51, the wire member 53, and the drive 70. Accordingly, the highest bending stiffness and the lowest bending stiffness of the insertion section 40 are restricted to a desired amount. The highest bending stiffness of the insertion section 40 is a bending stiffness that makes the insertion section 40 to be substantially straight, and does not include a bending stiffness of the insertion section 40 that is in a bent state due to an excessive pull of the wire member 53.

As shown in FIG. 1, the insertion apparatus 10 comprises an advance and retreat detection unit 60 that detects advances and retreats of the insertion section 40. The advance and retreat detection unit 60 outputs a result of the detection by the advance and retreat detection unit 60 to a stiffness controller (hereinafter referred to as a controller 121), which will be described later, arranged inside the insertion control apparatus 120. The advance and retreat detection unit 60 is arranged outside the subject 300, and is separate from the insertion section 40. Normally, the operator inserts the insertion section 40 from the entrance 301a of the tube portion 301 into the inside of the tube portion 301, grips the exposed part of the insertion section 40 exposed to the outside from the tube portion 301, and pushes the insertion section 40 from the gripped part. The exposed part is, for example, the proximal end portion of the insertion section 40. The advance and retreat detection unit 60 of the present embodiment detects an advance (push operation) of the insertion section 40 and a retreat (pull-back operation) of the insertion section 40 in the periphery of the gripped part. Accordingly, the advance and retreat detection unit 60 is arranged in the periphery of the exposed part of the insertion section 40 and the gripped part of the insertion section 40 exposed to the outside of the tube portion 301 of the subject 300. The advance and retreat detection unit 60 is arranged in, for example, the periphery of the entrance 301a of the tube portion 301. An advance of the insertion section 40 is made by, for example, a push operation of the insertion section 40, and a retreat of the insertion section 40 is made by, for example, a pull-back operation of the insertion section 40. Accordingly, the advance and retreat detection unit 60 detects an advance (push operation) of the insertion section 40 and a retreat (pull-back operation) of the insertion section 40 in the periphery of the entrance 301a.

The advance and retreat detection unit 60 includes a sensor 61. An amount of change of the sensor 61, for example, an amount of motion of the sensor 61 itself changes in accordance with an advance and retreat of the insertion section 40. The advance and retreat detection unit 60 also includes a detector 63 that detects an advance of the insertion section 40 or a retreat of the insertion section 40 in accordance with the amount of change of the sensor 61.

The sensor 61 includes, for example, a rotating member such as a roller, and the rotating member rotates in accordance with an advance and retreat of the insertion section 40. In this case, the detector 63 detects an advance of the insertion section 40 or a retreat of the insertion section 40 in accordance with the direction of rotation of the rotating member. The detector 63 includes, for example, an encoder.

The sensor 61 may include an emission portion that emits light toward a portion to be read on a surface of the insertion section 40, and a light receiving portion that receives a pattern of light reflected by the portion to be read on the surface. The emission portion is, for example, a light emission portion, such as a light source. The portion to be read is in a lattice-like pattern, for example, and is arranged on the surface. The reflection pattern differs in accordance with the position of the portion to be read. In this case, the detector 63 detects an advance of the insertion section 40 or a retreat of the insertion section 40 on the basis of the pattern of light received by the light receiving portion.

The detector 63 outputs a result of the detection to the controller 121, which will be described later, via a signal line (not shown in the drawings).

As shown in FIG. 1, the insertion apparatus 10 includes the controller 121 arranged in the insertion control apparatus 120. The controller 121 is configured by a hardware circuit including, for example, an ASIC, etc. The controller 121 may be configured by a processor. When the controller 121 is configured by a processor, a program code that causes the processor to function as the controller 121 when the processor is executed is stored in an internal or external memory (not shown in the drawings) that can be accessed by the processor.

When the advance and retreat detection unit 60 has detected an advance of the insertion section 40, the controller 121 controls the stiffness of the stiffness variable unit 50 to be a stiffness that makes the insertion section 40 passively bendable by an external force. The stiffness that makes the insertion section 40 passively bendable refers to a stiffness that allows the insertion section 40 to be passively bent by a reaction force applied to the insertion section 40 from a portion in contact with the tube portion 301. This stiffness is also a stiffness that allows the insertion section 40 to be bent along the shape inside of the tube portion 301. For example, when the advance and retreat detection unit 60 has detected an advance of the insertion section 40, the controller 121 decreases the stiffness of the stiffness variable unit 50 in such a manner that the bending stiffness of the insertion section 40 becomes lower while the insertion section 40 is advancing than the bending stiffness of the insertion section 40 while the insertion section 40 is retreating.

When the advance and retreat detection unit 60 has detected a retreat of the insertion section 40, the controller 121 controls the stiffness of the stiffness variable unit 50 to be a stiffness that makes the insertion section 40 substantially straight. For example, when the advance and retreat detection unit 60 has detected a retreat of the insertion section 40, the controller 121 increases the stiffness of the stiffness variable unit 50 in such a manner that the bending stiffness of the insertion section 40 becomes higher while the insertion section 40 is retreating than the bending stiffness of the insertion section 40 while the insertion section 40 is advancing. Specifically, the controller 121 increases the stiffness of the stiffness variable unit 50 in such a manner that the insertion section 40 is kept in a substantially straight state.

The stiffness that makes the insertion section 40 substantially straight refers to a stiffness that changes apart of the insertion section 40 including a bent part 203a (see FIG. 2B) to a substantially straight part 205a (see FIG. 2E), and that keeps the substantially straight part 205a in the substantially straight state without causing it to be bent, even when an external force such as a reaction force is applied to the substantially straight part 205a from a portion in contact with the tube portion 301. The external force refers to, for example, a force exerted on the substantially straight part 205a from a given angle with respect to the central axis of the substantially straight part 205a. The stiffness that makes the insertion section 40 substantially straight is higher than the stiffness that is not controlled by the controller 121. The substantially straight part 205a functions as a high stiffness part that is not bent and keeps the substantially straight state even if an external force is applied thereto. The other parts that are not controlled in stiffness function as low-stiffness parts that are passively bendable by an external force applied thereto. The stiffness that makes the insertion section 40 substantially straight can be adjusted to a desired value in accordance with the tube portion 301.

The controller 121 outputs a control signal that controls the stiffness of the stiffness variable unit 50 to the drive 70, which will be described later, via a signal line (not shown in the drawings).

As shown in FIG. 1, the insertion apparatus 10 includes the drive 70 that drives the stiffness variable unit 50 on the basis of a control instruction from the controller 121. The drive 70 is incorporated into, for example, the operation section 30. The drive 70 includes, for example, a motor 71 that is controlled by the controller 121 and generates a driving force, and a pulley 73 that is rotated by the driving force and pulls the wire member 53 toward the proximal end portion of the insertion section 40 by the rotation. The pulley 73 may press the wire member 53 toward the distal end portion of the insertion section 40 with a driving force.

An input apparatus (not shown in the drawings) is connected to the insertion control apparatus 120, and outputs a control start instruction to start operating, for example, the controller 121 to the controller 121. The input apparatus is a general input device, and is, for example, a button switch, a dial, etc.

[Working]

Hereinafter, an explanation will be given by taking the large intestine as an example of the tube portion 301. The operator grips the insertion section 40, for example, and inserts the distal end portion of the insertion section 40 from the entrance 301a (anus) of the large intestine into the inside of the large intestine. Next, the operator grips the proximal end portion of the insertion section 40 exposed to the outside from the large intestine, and pushes the insertion section 40 from the gripped part. Thereby, as shown in FIGS. 2A and 2B, the insertion section 40 is pushed toward a first bent portion 303a in the sigmoid colon of the large intestine that is present ahead of the entrance 301a, and is advanced toward the first bent portion 303a.

The advance and retreat detection unit 60 detects an advance of the insertion section 40, and outputs a result of the detection to the controller 121. The controller 121 outputs, to the drive 70, a control signal that controls the stiffness of the stiffness variable unit 50. The drive 70 drives the stiffness variable unit 50 on the basis of a control instruction from the controller 121. In this case, the drive 70 pushes the wire member 53 toward the distal end portion of the insertion section 40. The contraction of the sheath member 51 is released, and the sheath member 51 is extended by its elastic force. Accordingly, the sheath member 51 is decreased in stiffness, and the bending stiffness of the insertion section 40 is uniformly decreased in the entire part in which the sheath member 51 is arranged. Also, the insertion section 40 becomes passively bendable.

In FIG. 2A, in a state in which the insertion section 40 is decreased in stiffness and is passively bendable, the insertion section 40 advances toward the first bent portion 303*a* (shown in FIG. 2B). In this state, as shown in FIG. 2B, the insertion section 40 passes through the first bent portion 303*a*, advances toward a second bent portion 303*b* that is present in a deep portion of the first bent portion 303*a*, and passes through the second bent portion 303*b*. At this time, the insertion section 40 is inserted into the sigmoid colon and the descending colon of the large intestine in the shape of N.

In FIGS. 2A and 2B, the stiffness of the stiffness variable unit 50 is a stiffness that makes the insertion section 40 passively bendable, and the insertion section 40 pushed with a decreased bending stiffness is passively bendable by an external force applied from an inner wall of the large intestine. Accordingly, the insertion section 40 is allowed to pass through the first bent portion 303*a* of the sigmoid colon of the large intestine along the first bent portion 303*a*. This improves the smoothness of passage of the insertion section 40 through the first bent portion 303*a*. The insertion section 40 is passively bendable, the bending stiffness of the entire insertion section 40 is uniformly decreased, and the bending stiffness of the bent part 203*a* that is passing through the first bent portion 303*a* shown in FIG. 2B is decreased in a manner similar to the other parts of the insertion section 40. This suppresses overextension of the first bent portion 303*a* even if a push operation of the insertion section 40 is excessively performed, thus reducing the patient's distress.

Since some part of the large intestine is not fixed within the abdomen, the large intestine may be easily moved inside the abdomen by an advance of the insertion section 40. For example, when the distal end portion of the insertion section 40 is pushed in a state of having passed through the second bent portion 303*b* of the large intestine, the large intestine may be moved by the push. In this case, the hand side force of the operator who pushes the insertion section 40 may not be easily transmitted to the distal end portion of the insertion section 40, resulting in buckling of the insertion section 40. Such buckling further prevents the hand side force from being easily transmitted to the distal end portion of the insertion section 40, making it difficult to insert (advance) the distal end portion toward the deep portion. This may cause the insertion section 40 to be in a stuck state with a lower propulsion force, namely, result in decrease in insertability. For easy insertion of the insertion section 40, a procedure for substantial straightness that changes the large intestine to a substantially straight state by operating the insertion section 40 is known. However, acquisition of such a procedure for substantial straightness requires much training.

Figure 2C:
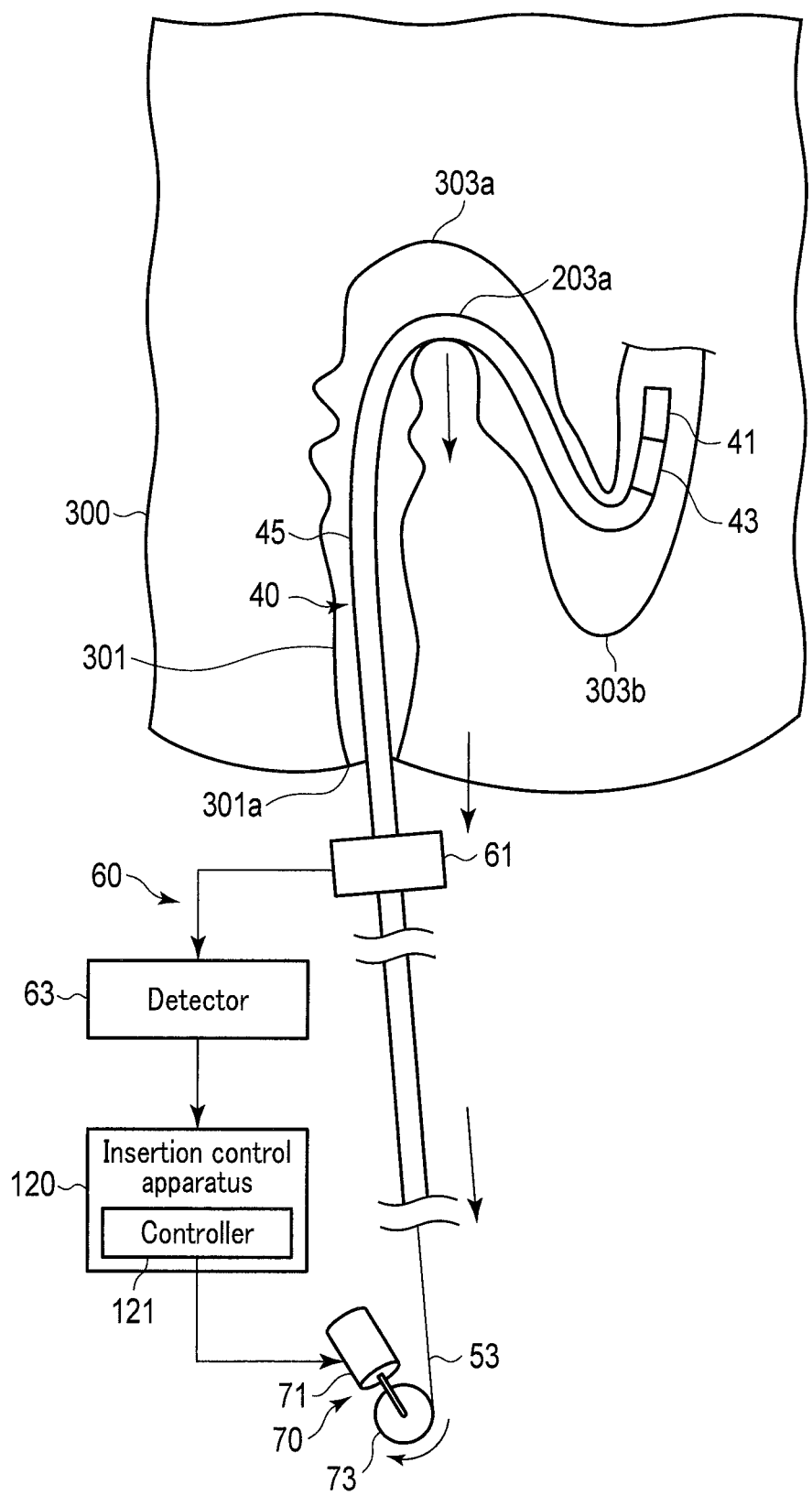
FIG. 2C is a diagram showing a state in which the insertion section shown in FIG. 2B is retreating.
Figure 2D:
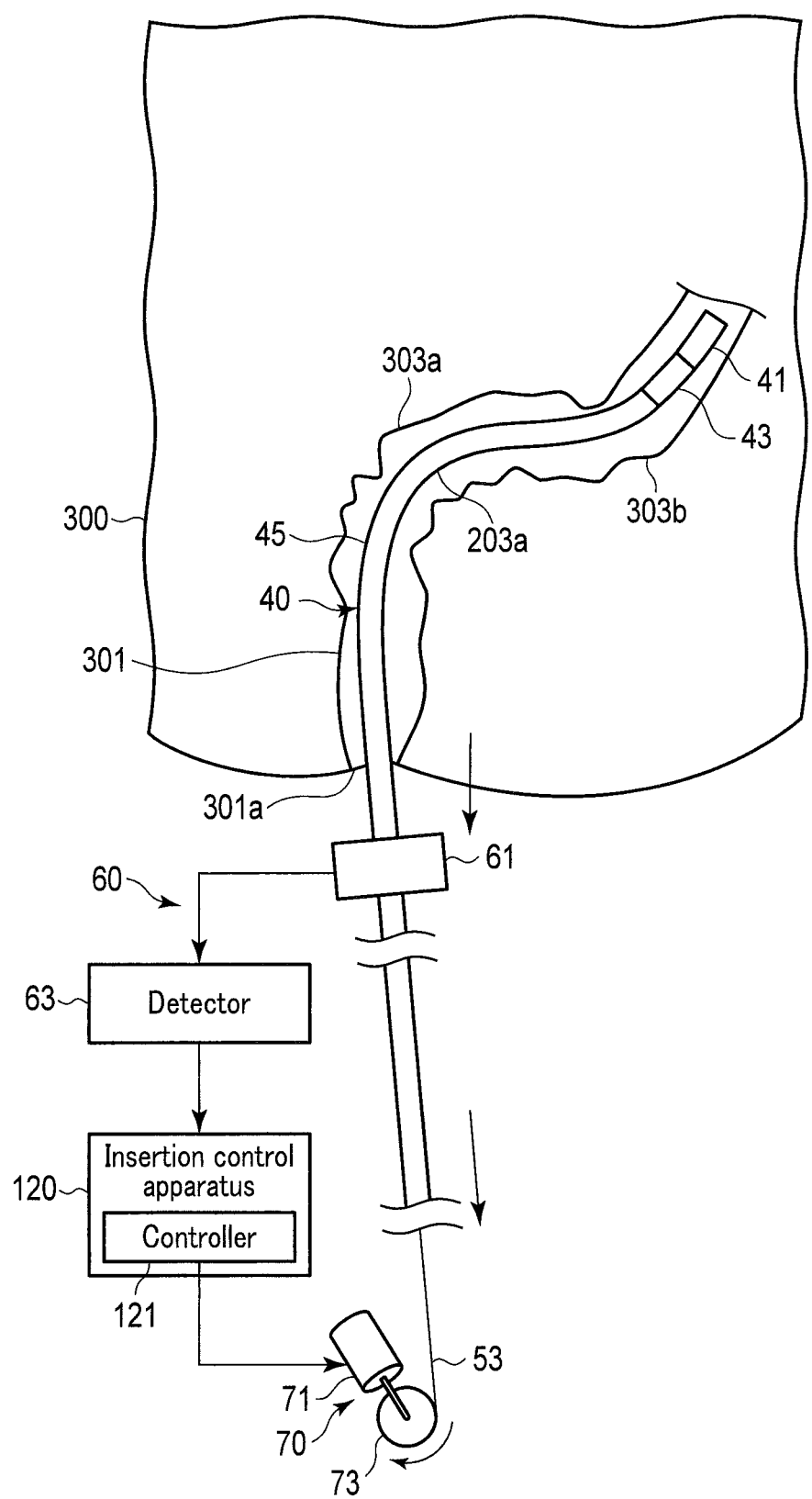
FIG. 2D is a diagram showing a state in which the insertion section shown in FIG. 2C is changed to a substantially straight state by the retreat of the insertion section.

Thus, in the present embodiment, a pull-back operation is performed after the insertion section 40 has passed through the second bent portion 303*b*. After the insertion section 40 is pulled back, as shown in FIG. 2C, the advance and retreat detection unit 60 detects a retreat of the insertion section 40, and outputs a result of the detection to the controller 121. The controller 121 outputs, to the drive 70, a control signal that controls the stiffness of the stiffness variable unit 50. The drive 70 drives the stiffness variable unit 50 on the basis of a control instruction from the controller 121. In this case, the drive 70 pulls the wire member 53 toward the proximal end portion of the insertion section 40. The wire member 53 pulls the sheath member 51 toward the proximal end portion of the insertion section 40 by being pulled by the drive 70, and the sheath member 51 is contracted toward the proximal end portion of the sheath member 51 by being pulled by the wire member 53. Accordingly, the stiffness of the sheath member 51 is increased to a stiffness that makes the insertion section 40 substantially straight, and the bending stiffness of the insertion section 40 is uniformly increased in the entire part in which the sheath member 51 is arranged. At this time, the bending stiffness of the bent part 203*a* is increased in a manner similar to the other parts of the insertion section 40. Thereby, as shown in FIGS. 2D and 2E, a radius of curvature of the insertion section 40 increases at a part including the bent part 203*a*, and the part of the insertion section 40 including the bent part 203*a* changes from a bent state to a substantially straight state. That is, the part of the insertion section 40 including the bent part 203*a* changes to the substantially straight part 205*a*. In accordance with this change, the part of the large intestine including the first bent portion 303*a* and the second bent portion 303*b* changes to a substantially straight state. That is, the part of the large intestine including the first bent portion 303*a* changes to a substantially straight portion 305*a*. Likewise, the part of the large intestine including the second bent portion 303*b* changes to a substantially straight part.

When the insertion section 40 has stopped the retreat, as shown in FIG. 2E, the controller 121 receives an input indicating the stop from the advance and retreat detection unit 60, and outputs a control signal that stops the drive 70 to the drive 70. The drive 70 stops the driving, and keeps the wire member 53 in a pulled state. Accordingly, the sheath member 51 keeps the contraction, and the insertion section 40 is kept in the substantially straight state.

When the insertion section 40 in the substantially straight state is pushed, the insertion section 40 is easily inserted into the large intestine in the substantially straight state toward the deep portion. When the insertion section 40 is pushed again, the advance and retreat detection unit 60 detects an advance of the insertion section 40. The controller 121, the drive 70, and the stiffness variable unit 50 repeat the above-described operations.

The insertion section 40 is in a substantially straight state, and the hand side force is efficiently transmitted from the gripped part to the distal end portion of the insertion section 40. This improves the insertability of the insertion section 40 toward the deep portion, without causing the substantially straight part 205*a* with a high bending stiffness to be bent, even if an external force is applied to the insertion section 40 from the tube portion 301. Occurrence of buckling is suppressed by efficient transmission of the force and the substantially straight part 205*a* with a high bending stiffness.

[Advantages]

In the present embodiment, the advance and retreat detection unit 60 detects an advance and retreat of the insertion section 40. When the insertion section 40 has advanced, the controller 121 controls the stiffness of the stiffness variable unit 50 to be a stiffness that makes the insertion section 40 passively bendable, and decreases the stiffness of the stiffness variable unit 50. In this case, when the insertion section 40 is pushed, the insertion section 40 can be passively bent by an external force applied to an inner wall of the large intestine, and can pass through the first bent portion 303a of the sigmoid colon of the large intestine along the first bent portion 303a. This improves the smoothness of passage of the insertion section 40 through the first bent portion 303a. When the insertion section 40 is retreated, the controller 121 controls the stiffness of the stiffness variable unit 50 to a stiffness that makes the insertion section 40 have a substantially straight stiffness. In this case, the part of the insertion section 40 including the bent part 203a changes from a bent state to a substantially straight state. In accordance with this change, portions of the large intestine including the first bent portion 303a and the second bent portion 303b also change to a substantially straight state. Accordingly, by pushing the insertion section 40 in the substantially straight state, the insertion section 40 in the substantially straight state can be easily inserted toward a deep portion of the large intestine in the substantially straight state, and the insertability of the insertion section 40 through the deep portion of the tube portion 301 can be improved. At this time, the insertion section 40 is in a substantially straight state, and the large intestine is also in a substantially straight state. Accordingly, the hand side force that pushes the insertion section 40 is easily transmitted to the distal end portion of the insertion section 40. This prevents buckling of the insertion section 40, and improves the insertability of the insertion section 40 into a deep portion of the tube portion 301.

In the present embodiment, the operator does not need to adjust the bending stiffness of the insertion section 40, and can focus on the push operation or pull-back operation of the insertion section 40. It is thereby possible in the present embodiment to improve the operability at the time of inserting the insertion section 40 into a deep portion of the tube portion 301. In the present embodiment, since an overtube is not used, the insertion section 40 is prevented from increasing in outer diameter, thus reducing the patient's distress and burden.

In the present embodiment, it is possible to reduce the level of difficulty in acquiring the procedure for substantial straightness that requires much training, and to support the procedure for substantial straightness.

In the present embodiment, the advance and retreat detection unit 60 is arranged outside the subject 300. This prevents the insertion section 40 from increasing in outer diameter, and the insertability of the insertion section 40 into a deep portion of the tube portion 301 can be further improved. The advance and retreat detection unit 60 is arranged in the periphery of both the exposed part and the gripped part. Accordingly, the advance and retreat of the insertion section 40 at the hand side can be reliably detected. In the present embodiment, the advance and retreat of the insertion section 40 can be detected by a simple configuration including the sensor 61 and the detector 63.

In the present embodiment, the stiffness variable unit 50 uniformly changes the bending stiffness of the entire insertion section 40. Accordingly, the bending stiffness of the insertion section 40, for example, can be uniformly decreased, and overextension of the first bent portion 303a can be suppressed even if a push operation of the insertion section 40 is excessively performed, thus reducing the patient's distress. For example, the bending stiffness of the insertion section 40 can be uniformly increased, and most of the sigmoid colon of the large intestine can be changed to a substantially straight state.

The advance and retreat detection unit 60 may detect a direction of rotation around the axis of the insertion section 40. This rotation represents a twist. The rotating member rotated by the twist is separate from a rotating member that detects an advance and retreat. In this case, when the distal end portion of the insertion section 40 is viewed from the proximal end portion, the clockwise direction is defined as a right rotation, and the counterclockwise direction is defined as a left rotation. The controller 121 controls the stiffness of the stiffness variable unit 50 to be a stiffness that makes the insertion section 40 passively bendable when at least one of an advance and a right rotation of the insertion section 40, for example, is detected by the advance and retreat detection unit 60. When the advance and retreat detection unit 60 has detected at least one of a retreat and a left rotation of the insertion section 40, the controller 121 controls the stiffness of the stiffness variable unit 50 to a stiffness that makes the insertion section 40 substantially straight. Thereby, it is possible in the present embodiment to further support the procedure for substantial straightness.

[First Variant]

A first variant of the first embodiment will be explained with reference to FIGS. 3, 4A, 4B, and 4C. In the present variant, only the features different from those of the first embodiment will be described.

[Configuration]

Figure 3:
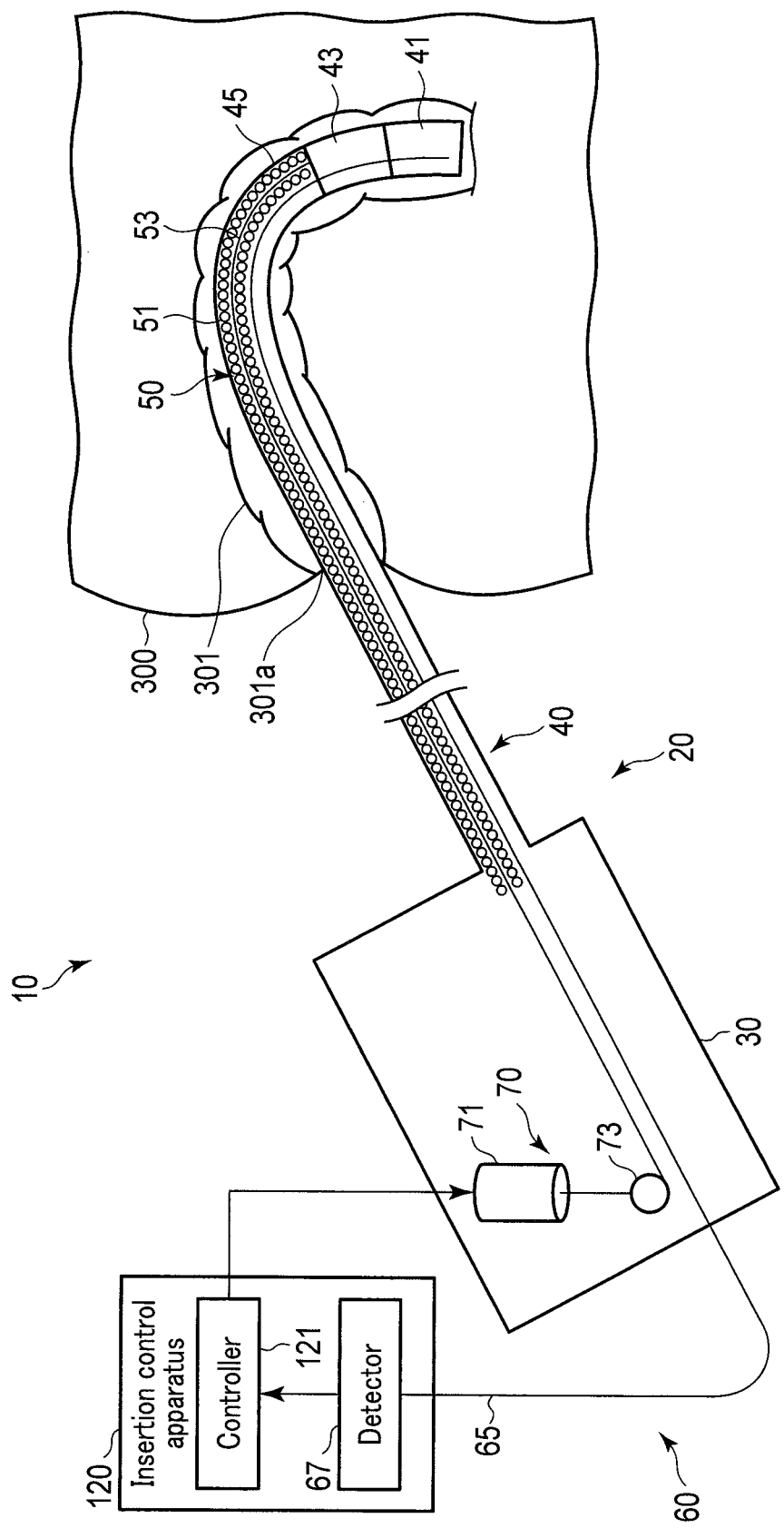
FIG. 3 is a schematic diagram of a flexible tube insertion apparatus according to a first variant of the first embodiment.

As shown in FIG. 3, an advance and retreat detection unit 60 includes a shape detection portion 65 that detects a shape of the insertion section 40, and a detector 67 that detects an advance of the insertion section 40 or a retreat of the insertion section 40 on the basis of a change in shape of the insertion section 40 in accordance with a push operation or a pull-back operation of the insertion section 40.

The shape detection portion 65 is incorporated into, for example, the insertion section 40. The shape detection portion 65 is juxtaposed to a stiffness variable unit 50. The shape detection portion 65 includes, for example, at least one of a coil, an optical fiber sensor, an acceleration sensor, and an absorption member. The coil generates a magnetic field in accordance with the shape of the insertion section 40. The optical fiber sensor changes in transmittance of light in accordance with the shape of the insertion section 40. The absorption member absorbs X-rays in accordance with the shape of the insertion section 40.

The shape detection portion 65 constantly performs a detection (operation) after a detection start instruction output from the input apparatus is input to the shape detection portion 65. The detection timing may be every predetermined passage of time, and is not particularly limited. The shape detection portion 65 is connected to the detector 67 by wire or by wireless, for example, and a result of the detection by the state detection portion 65 is output to the detector 67.

Figure 4B:
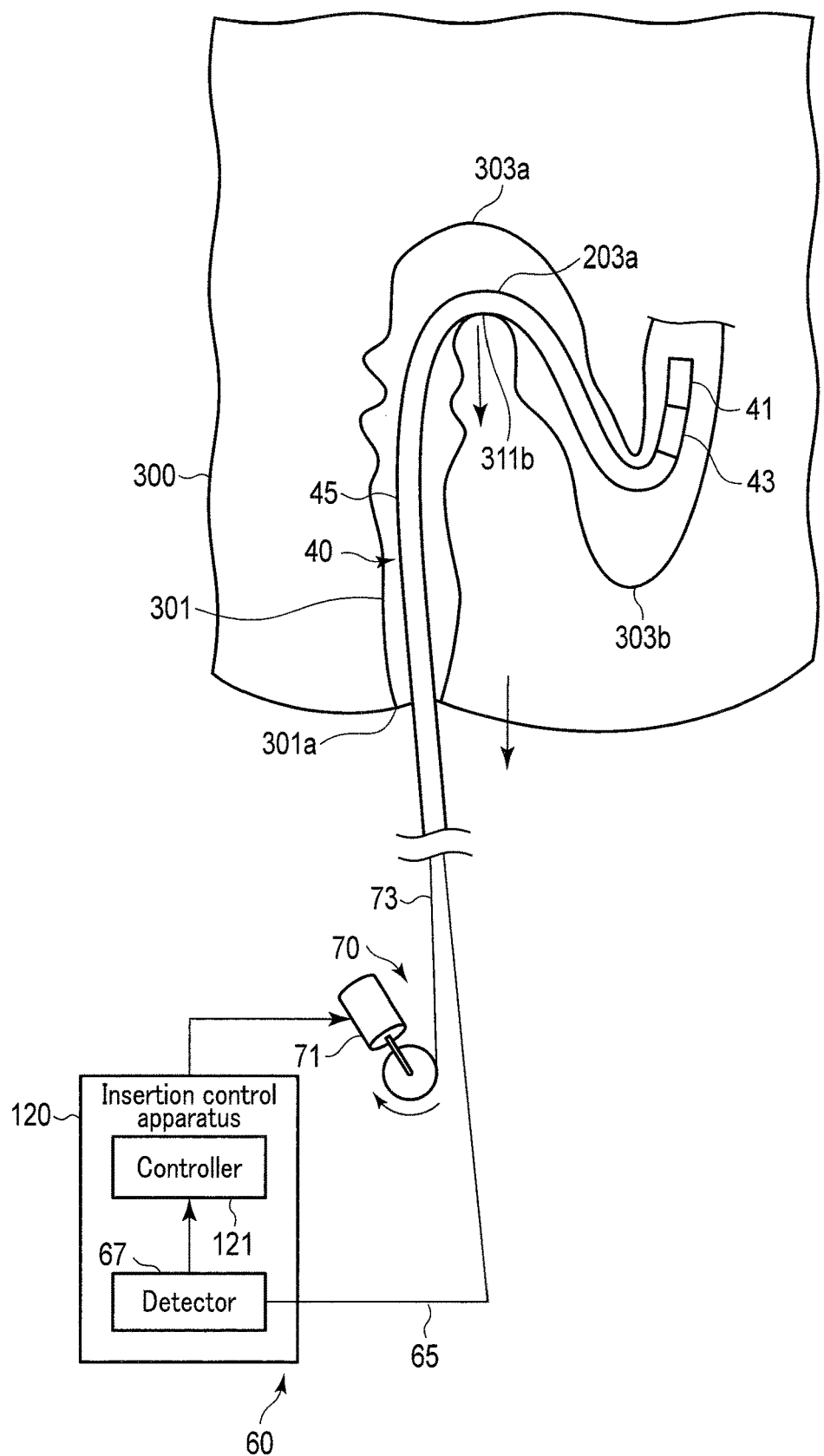
FIG. 4B is a diagram showing a state in which the insertion section shown in FIG. 4A is retreating.

The detector 67 detects whether or not a looped bent part 203a (see FIG. 4A) is formed in the insertion section 40, on the basis of the shape of the insertion section 40. The bent part 203a in the present variant includes, for example, a U-shaped bent part of the insertion section 40 that is bent in an approximate U shape, as well as a part that is wound to curve back toward itself. Normally, as shown in FIG. 4A, when the distal end portion of the insertion section 40 passes through the first bent portion 303a, a looped bent part 203a is generated at a passing part of the insertion section 40 that is passing through the first bent portion 303a. In a state in which a push operation is performed and the bent part 203a is made to abut against an outer peripheral wall 311a of the inside the first bent portion 303a, as shown in FIG. 4A, the shape of the bent part 203a is generated by the push operation and is gradually increased. In other words, the radius of curvature of the bent part 203a is decreased by the push operation. In a state in which a pull-back operation is performed and the bent part 203a is made to abut against an inner peripheral wall 311b inside the first bent portion 303a, as shown in FIG. 4B, the shape of the bent part 203a is gradually reduced and eliminated by the push operation. In other words, the radius of curvature of the bent part 203a is increased by the pull-back operation. Thus, the shape of the bent part 203a changes in accordance with a push operation or a pull-back operation. Accordingly, the detector 67 detects an advance of the insertion section 40 or a retreat of the insertion section 40 on the basis of a change in shape of the bent part 203a.

To detect a change in shape of the bent part 203a, the detector 67 detects a radius of curvature of the bent part 203a in the insertion section 40 on the basis of, for example, the shape of the insertion section 40. The detector 67 detects whether or not the radius of curvature is decreasing or increasing.

If the radius of curvature is decreasing, the detector 67 detects that the bent part 203a has been generated, a push operation has been performed, and that the insertion section 40 is advancing. That is, the detector 67 detects an advance of the insertion section 40 when the shape of the bent part 203a in the insertion section 40 is increased by a push operation.

If the radius of curvature is increasing, the detector 67 detects that the bent part 203a is decreasing, that a pull-back operation has been performed, and that the insertion section 40 is retreating. That is, the detector 67 detects a retreat of the insertion section 40 when the shape of the bent part 203a in the insertion section 40 is reduced by a pull-back operation.

The detector 67 may compare a threshold value set to a desired value in advance and a radius of curvature. If the radius of curvature is greater than a threshold value, the detector 67 detects that the bent part 203a has been eliminated, a pull-back operation has been performed, and that the insertion section 40 is retreating. If the radius of curvature is less than the threshold value, the detector 67 detects that the bent part 203a has been generated, a push operation has been performed, and that the insertion section 40 is advancing.

In the present embodiment, the advance and retreat detection unit 60 detects an advance (push operation) of the insertion section 40 and a retreat (pull-back operation) of the insertion section 40 at a passing part (bent part 203a) of the insertion section 40 that is passing through the first bent portion 303a, unlike the first embodiment.

The detector 67 is configured by a hardware circuit including, for example, an ASIC, etc. The detector 67 may be configured by a processor. When the detector 67 is configured by a processor, a program code that causes the processor to function as the detector 67 when the processor is executed is stored in an internal or external memory (not shown in the drawings) that can be accessed by the processor. The detector 67 is arranged in the insertion control apparatus 120. The detector 67 and the controller 121 may be configured using one processor, or may be configured using a plurality of processors. In the latter case, the processors may perform processing in association with each other, so as to transmit and receive data to and from each other. Furthermore, the processors may be arranged in different housings in the latter case.

In a state in which a result detected by the shape detection portion 65 is input, the detector 67 constantly performs a detection (operation) after a detection start instruction output from the input apparatus is input to the detector 67. The detection timing may be every predetermined passage of time, and is not particularly limited. The detector 67 outputs a result of detection to the controller 121, via a signal line (not shown in the drawings).

[Working]

As shown in FIG. 4A, when the insertion section 40 passes through the first bent portion 303a for insertion into a deep portion, a looped bent part 203a is generated at a passing part of the insertion section 40 that is passing through the first bent portion 303a. In this case, the bent part 203a is made to abut against the outer peripheral wall 311a inside the first bent portion 303a by a push operation. In this case, the radius of curvature of the bent part 203a is decreased by the abutment. The detector 67 detects that the radius of curvature is decreased via the shape detection portion 65. The detector 67 detects an advance of the insertion section 40, and outputs a result of the detection to the controller 121. The controller 121 outputs, to the drive 70, a control signal that controls the stiffness of the stiffness variable unit 50. The drive 70 and the stiffness variable unit 50 are driven in a manner similar to the first embodiment. Accordingly, the bending stiffness of the insertion section 40 is uniformly decreased in the entire part in which the sheath member 51 is arranged. The bending stiffness of the bent part 203a is decreased in a manner similar to the other parts of the insertion section 40.

The stiffness of the stiffness variable unit 50 is a stiffness that makes the insertion section 40 passively bendable, and the insertion section 40 that is pushed with a decreased bending stiffness is passively bendable by an external force applied from an inner wall of the large intestine. Accordingly, the insertion section 40 is allowed to pass through the first bent portion 303a of the sigmoid colon of the large intestine along the first bent portion 303a. This improves the smoothness of passage of the insertion section 40 through the first bent portion 303a. The insertion section 40 is passively bendable, the bending stiffness of the entire insertion section 40 is uniformly decreased, and the bending stiffness of the bent part 203a that is passing through the first bent portion 303a is decreased in a manner similar to the other parts of the insertion section 40. This suppresses overextension of the first bent portion 303a even if a push operation of the insertion section 40 is excessively performed, thus reducing the patient's distress.

Figure 4C:
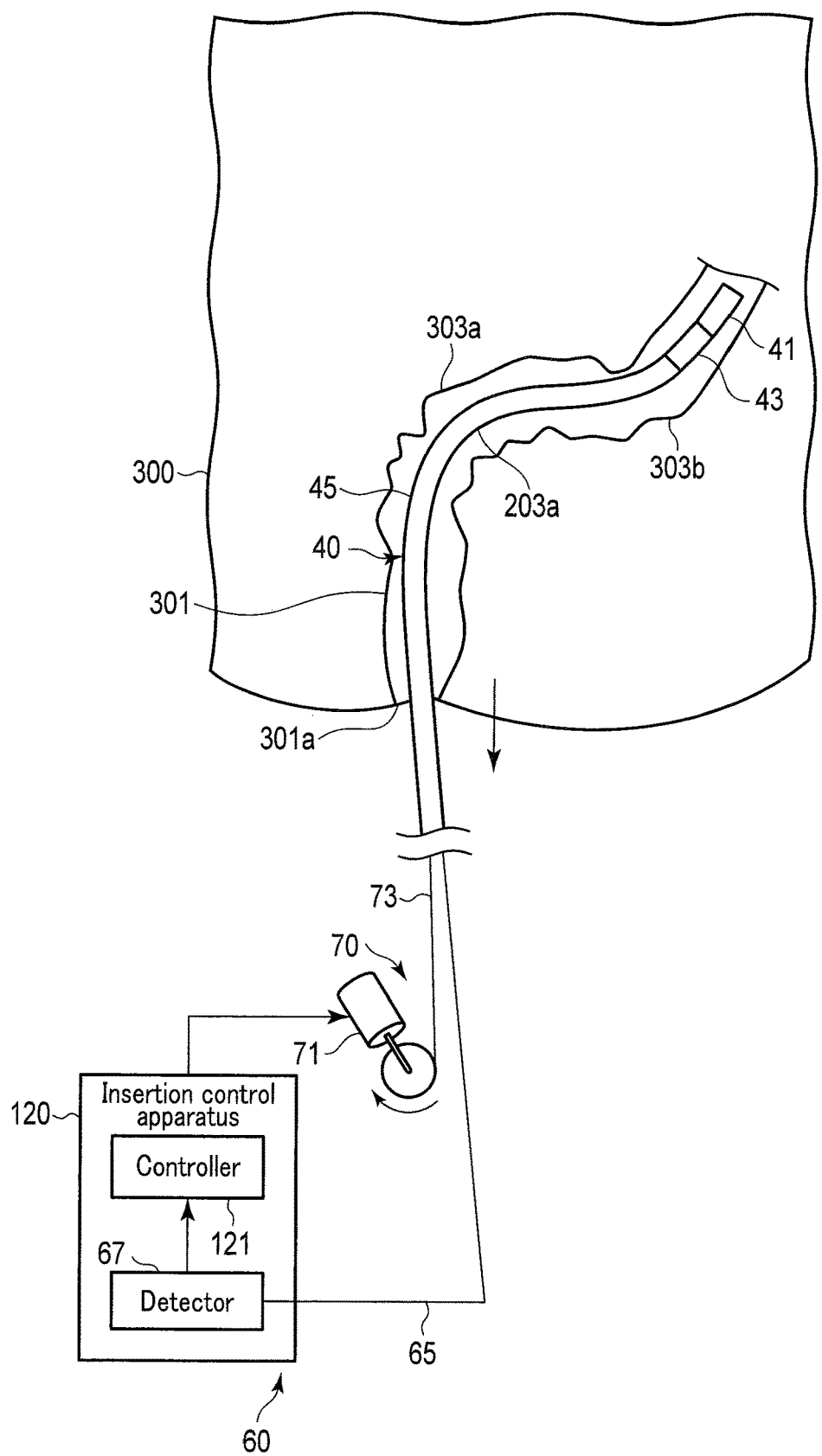
FIG. 4C is a diagram showing a state in which the insertion section shown in FIG. 4B is changed to a substantially straight state by the retreat of the insertion section.
Figure 4D:
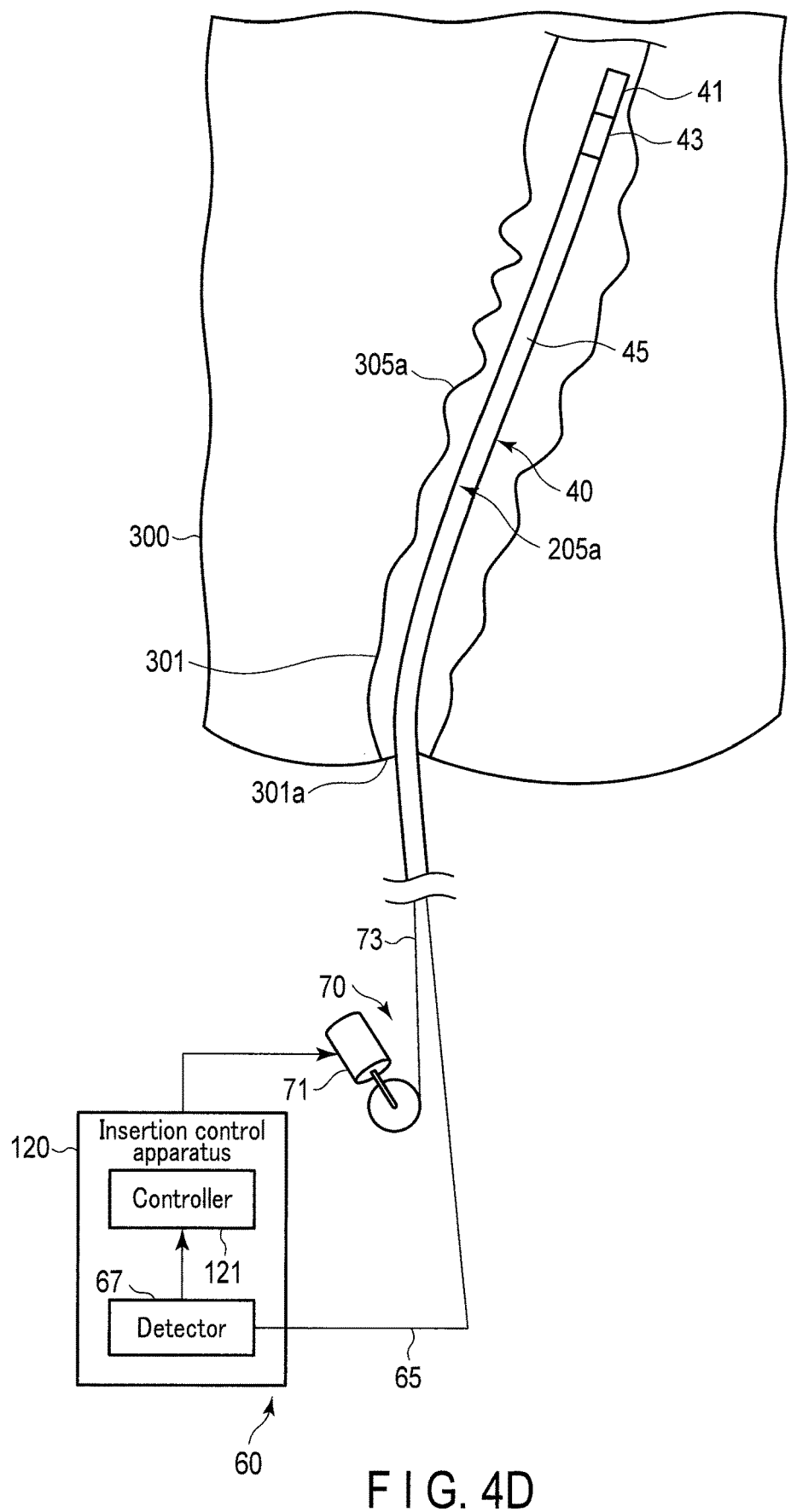
FIG. 4D is a diagram showing a state in which the insertion section shown in FIG. 4C is changed to a substantially straight state by the retreat of the insertion section.

As shown in FIG. 4B, when the insertion section 40 that is passing through the first bent portion 303a is pulled back, the bent part 203a is made to abut against the inner peripheral wall 311b inside the first bent portion 303a by the pull-back operation. In this case, the radius of curvature of the bent part 203a is increased by the abutment. The detector 67 detects that the radius of curvature is increased via the shape detection portion 65. The detector 67 detects a retreat of the insertion section 40, and outputs a result of the detection to the controller 121. The controller 121 outputs, to the drive 70, a control signal that controls the stiffness of the stiffness variable unit 50. The drive 70 and the stiffness variable unit 50 are driven in a manner similar to the first embodiment. Accordingly, the stiffness of the sheath member 51 is increased to a stiffness that makes the insertion section 40 substantially straight, and the bending stiffness of the insertion section 40 is uniformly increased in the entire part in which the sheath member 51 is arranged. At this time, the bending stiffness of the bent part 203a is increased in a manner similar to the other parts of the insertion section 40. Thereby, the radius of curvature of the insertion section 40 including the bent part 203a is increased. As shown in FIGS. 4C and 4D, the part of the insertion section 40 including the bent part 203a is changed to the substantially straight part 205a. In accordance with this change, a portion of the large intestine including the first bent portion 303a and the second bent portion 303b is changed to the substantially straight portion 305a.

[Advantages]

In the present variant, the advance and retreat detection unit 60 detects an advance (push operation) of the insertion section 40 and a retreat (pull-back operation) of the insertion section 40 at the passing part (bent part 203a) of the insertion section 40 that is passing through the first bent portion 303a. Accordingly, in the present variant, an advance and retreat of the insertion section 40 at the bent part 203a can be detected, and the entire insertion section 40 can be varied to a passively bendable state or a substantially straight state, in accordance with the situation of the bent part 203a.

The detector 67 may calculate state information of the insertion section 40 on the basis of the result of the detection by the shape detection portion 65. The state information of the insertion section 40 calculated by the detector 67 includes, for example, shape information, twist information, and position information of the insertion section 40. The detector 67 is connected to a display apparatus 140, and outputs a calculation result calculated by the detector 67 to the display apparatus 140. The display apparatus 140 displays current state information of the insertion section 40 in the tube portion 301 on the basis of the calculation result calculated by the detector 67. The current state information of the insertion section 40 in the tube portion 301 is the combined information of state information of the insertion section 40 and state information of the tube portion 301. The state information of the tube portion 301 includes, for example, shape information of the tube portion 301 and position information of the first bent portion 303a and the second bent portion 303b in the tube portion 301. The state information of the tube portion 301 is calculated by the detector 67 on the basis of the state information of the insertion section 40. The display is performed in a three-dimensional manner, for example. The operator is capable of monitoring the position and state of the insertion section 40 in the tube portion 301 on the basis of the state information of the insertion section 40 displayed on the display apparatus 140.

[Second Variant]

A second variant of the first embodiment will be explained with reference to FIGS. 5, 6A, 6B and 6C. In the present variant, only the features different from those of the first variant of the first embodiment will be described.

[Configuration]

A flexible tube 45 of an insertion section 40 is divided into a plurality of segments 47 arranged in a column shape along an axis direction of the insertion section 40. The segments 47 may function as non-existent virtual regions, or may function as existent structures.

The bending stiffness of each segment 47 can be independently changed under control of the controller 121. The bending stiffness of the flexible tube 45 may be partially changed by the bending stiffness of the segments 47 independently controlled by the controller 121.

The segments 47 are obtained by dividing the flexible tube 45, but are not limited thereto, and the segments 47 may be obtained by dividing the insertion section 40. It is thereby possible to partially change the bending stiffness of the insertion section 40 in accordance with the bending stiffness of each of the segments 47 independently controlled by the controller 121.

In the present variant, the stiffness variable unit 50 includes one or more stiffness variable portions 55 that change in stiffness. The stiffness variable portions 55 are incorporated into the respective segments 47. The stiffness variable portions 55 may be incorporated into all the segments 47, or may be incorporated into only some of the segments 47. The area at which the stiffness variable portion 55 is provided may function at least as the segment 47. One stiffness variable portion 55 may be integrally incorporated into a plurality of segments 47. The stiffness variable portions 55 may be arranged in a line along the axis direction of the insertion section 40, or may be arranged in a plurality of lines. When the stiffness variable portions 55 are arranged in a plurality of lines, the stiffness variable portions 55 may be provided at the same position in such a manner that the stiffness variable portions 55 are adjacent to each other as viewed in a circumferential direction of the flexible tube 45, or may be provided so as to be shifted as viewed in the axis direction of the insertion section 40. The stiffness variable portions 55 are only required to vary the bending stiffness of the insertion section 40 in units of the segments 47, in accordance with the stiffness of the stiffness variable portions 55.

Although not shown, the stiffness variable portion 55 is configured by, for example, an actuator including a coil pipe formed by a metal line and a conductive electroactive polymer artificial muscle (hereinafter referred to as EPAM) sealed inside the coil pipe. The central axis of the coil pipe is provided to match the central axis of the insertion section 40, or in parallel therewith. The coil pipe includes electrodes provided on both end portions of the coil pipe.

The electrodes of the stiffness variable portion 55 are connected to the insertion control apparatus 120 via a signal cable 57 incorporated into the endoscope 20, and receive electric power supplied from the insertion control apparatus 120. When a voltage is applied to the EPAM via the electrodes, the EPAM tries to extend and contract along the central axis of the coil pipe. However, the EPAM is restricted from extending and contracting by the coil pipe. This changes the stiffness of the stiffness variable portion 55. The stiffness of the stiffness variable portion 55 increases as the value of the applied voltage increases. When the stiffness of the stiffness variable portion 55 changes, the bending stiffness of the segments 47 incorporating the stiffness variable portions 55 also changes in accordance therewith. Electric power is independently supplied to the respective electrodes. Accordingly, the stiffness variable portions 55 independently change in stiffness, and the segments 47 also independently change in bending stiffness. In this manner, the stiffness variable portions 55 change the bending stiffness of the segments 47 in accordance with the change in stiffness of the stiffness variable portions 55, and partially change the bending stiffness of the flexible tube 45 in accordance with the change in bending stiffness of the segments 47.

As the stiffness variable portion 55, a shape memory alloy may be used, instead of the EPAM.

The controller 121 of the present variant controls the stiffness of the stiffness variable portion 55 corresponding to the segments 47 arranged at least in the bent part 203a.

The drive 70 individually drives the stiffness variable portions 55 corresponding to the segments 47 arranged at least in the bent part 203a to have different stiffnesses. The drive 70 is a power supplying portion that supplies electric power to the respective stiffness variable portions 55. The drive 70 is, for example, a power source arranged in the insertion control apparatus 120.

[Working]

When the insertion section 40 is inserted into a deep portion through the first bent portion 303a, as shown in FIG. 6A, a looped bent part 203a is generated at a passing part of the insertion section 40 that is passing through the first bent portion 303a. In this case, the bent part 203a is made to abut against the outer peripheral wall 311a inside the first bent portion 303a by a push operation. In this case, the radius of curvature of the bent part 203a is decreased by the abutment. The detector 67 detects that the radius of curvature is decreased via the shape detection portion 65. The detector 67 detects an advance of the insertion section 40. The detector 67 outputs position information of the bent part 203a in the insertion section 40, as well as a result of the detection, to the controller 121. The controller 121 outputs, to the drive 70, a control signal that controls the stiffness of the stiffness variable unit 50. The drive 70 drives the stiffness variable portion 55 in such a manner that the stiffness of the stiffness variable portions 55 corresponding to the segments 47 arranged at least in the bent part 203a decreases. In accordance therewith, the bending stiffness of the bent part 203a, which is a passing part that is passing through the first bent portion 303a, is also decreased. In the present variant, the bending stiffness of the insertion section 40 is not uniformly decreased in the entire part of the insertion section 40 in which the stiffness variable unit 50 is arranged, unlike the first embodiment and the first variant. In the present variant, the bending stiffness of at least the bent part 203a, which is a passing part, is uniformly decreased.

At this time, the stiffness of the stiffness variable portion 55, which is located in the bent part 203a, is a stiffness that makes the bent part 203a passively bendable, and the bent part 203a that is pushed with a decreased bending stiffness is passively bendable by an external force applied from the inner wall of the large intestine. Accordingly, the bent part 203a is allowed to pass through the first bent portion 303a of the sigmoid colon of the large intestine along the first bent portion 303a. This improves the smoothness of passage of the bent part 203a through the first bent portion 303a. The bent part 203a is passively bendable, and the bending stiffness of the bent part 203a is decreased. This suppresses overextension of the first bent portion 303a even if a push operation of the bent part 203a is excessively performed, thus reducing the patient's distress.

Figure 6B:
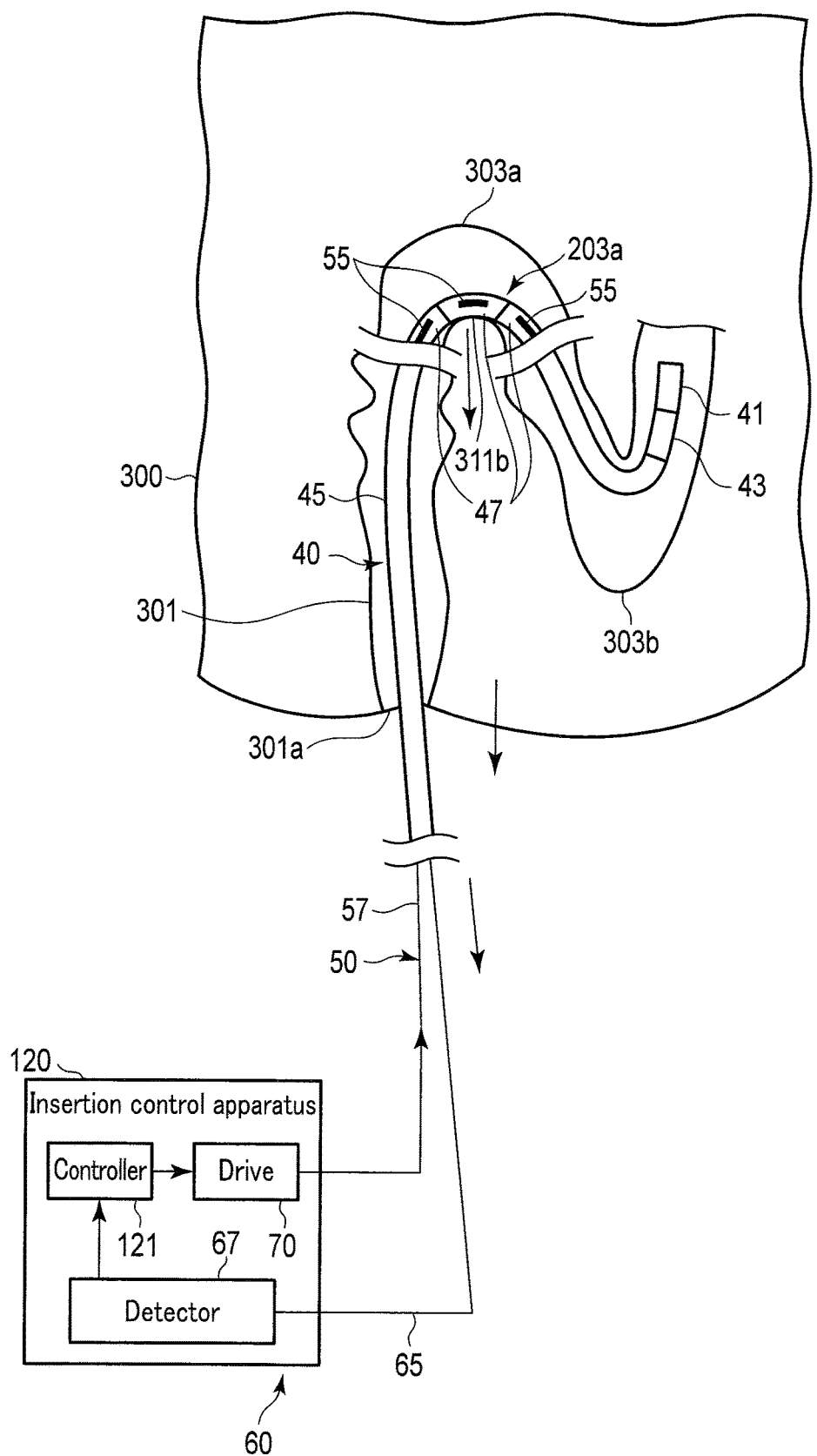
FIG. 6B is a diagram showing a state in which the insertion section shown in FIG. 6A is retreating.

As shown in FIG. 6B, when the insertion section 40 that is passing through the first bent portion 303a is pulled back, the bent part 203a is made to abut against the inner peripheral wall 311b inside the first bent portion 303a by the pull-back operation. In this case, the radius of curvature of the bent part 203a is increased by the abutment. The detector 67 detects that the radius of curvature is increased via the shape detection portion 65. The detector 67 detects a retreat of the insertion section 40. The detector 67 outputs position information of the bent part 203a in the insertion section 40, as well as a result of the detection, to the controller 121. The controller 121 outputs, to the drive 70, a control signal that controls the stiffness of the stiffness variable unit 50. The drive 70 drives the stiffness variable portion 55 in such a manner that the stiffness of the stiffness variable portions 55 corresponding to the segments 47 arranged at least in the bent part 203a is increased. Such stiffness variable portions 55 are indicated in black in FIGS. 6B, 6C, and 6D. Thereby, the stiffness of the stiffness variable portions 55 located at least in the bent part 203a is increased, and the bending stiffness of the bent part 203a, which is a passing part that is passing through the first bent portion 303a, is also increased. In the present variant, the bending stiffness of the insertion section 40 is not uniformly decreased in the entire part of the insertion section 40 in which the stiffness variable unit 50 is arranged, unlike the first embodiment and the first variant. In the present variant, the bending stiffness of at least the bent part 203a, which is a passing part, is uniformly increased.

Figure 6D:
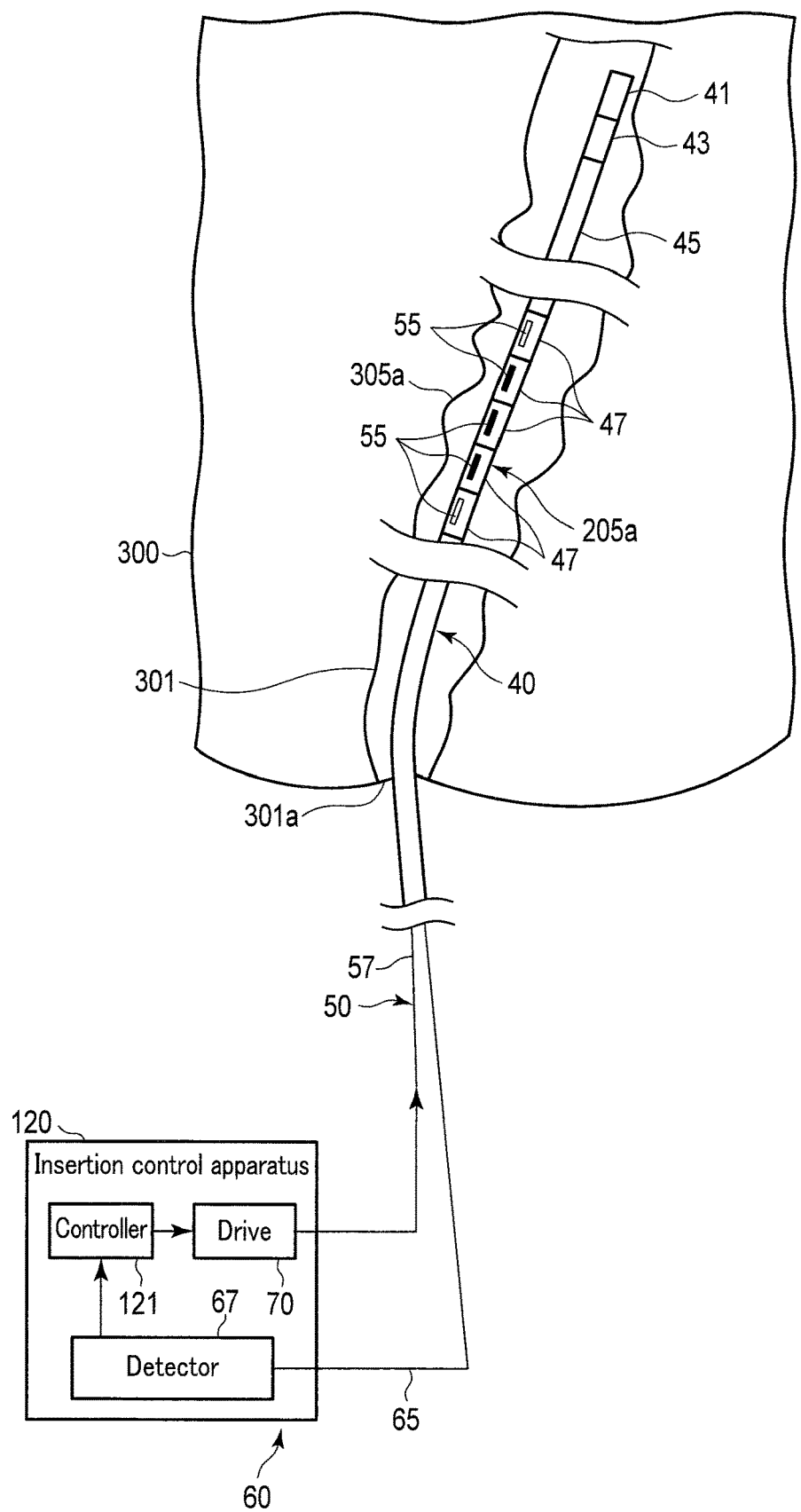
FIG. 6D is a diagram showing a state in which the insertion section shown in FIG. 6C is changed to a substantially straight state by the retreat of the insertion section.

At this time, the stiffness of the stiffness variable portion 55 located at the bent part 203a is increased to a stiffness that makes the bent part 203a substantially straight, and the bending stiffness of the bent part 203a is increased. Thereby, the radius of curvature of the bent part 203a is increased. Moreover, as shown in FIGS. 6C and 6D, the bent part 203a is changed to the substantially straight part 205a. In accordance with this change, the first bent portion 303a is changed to the substantially straight portion 305a.

After the insertion section 40 has stopped retreating, the controller 121 receives an input indicating the stop from the advance and retreat detection unit 60, and outputs a control signal that stops the drive 70 to the drive 70. The drive 70 stops supplying electric power, and keeps the stiffness of the stiffness variable portion 55. Accordingly, the insertion section 40 is kept in a substantially straight state.

The large intestine includes a plurality of bent portions. Herein, let us assume that the insertion section 40 includes a plurality of bent parts, and that the bent parts are arranged in the respective bent portions. In the present variant, the stiffness of the stiffness variable portions 55 arranged in the respective bent parts may be simultaneously varied, or may be varied in accordance with a desired pattern. Not all the stiffness variable portions 55 need to be varied in stiffness, and only some of them may be varied in accordance with an input instruction from the input apparatus, for example.

[Advantages]

In the present variant, the bent part 203a can be varied to a passively bendable state or a substantially straight state, in accordance with the situation of at least the bent part 203a.

In the present variant, the controller 121 controls the stiffness of the stiffness variable portions 55 corresponding to the segments 47 arranged in the bent part 203a. Accordingly, the bending stiffness of the insertion section 40 can be accurately controlled.

The present invention is not limited to the above-described embodiment and can be embodied in practice by modifying the structural elements without departing from the gist of the invention. In addition, various inventions can be made by suitably combining the structural elements disclosed in connection with the above embodiment.

Additional advantages and variants will readily occur to those skilled in the art. Therefore, the invention in its broader aspects is not limited to the specific details and representative embodiments shown and described herein. Accordingly, various variants may be made without departing from the spirit or scope of the general inventive concept as defined by the appended claims and their equivalents.

What is claimed is:

1. A flexible tube insertion apparatus comprising:
an insertion section including a distal end and a proximal end, the insertion section being configured to be inserted into a subject from the distal end;
a stiffness variable unit that is provided in the insertion section, the stiffness variable unit being configured to change a bending stiffness of the insertion section;
an advance and retreat sensor configured to detect an advance that is a movement toward a direction of the distal end of the insertion section and a retreat that is a movement toward a direction of the proximal end of the insertion section; and a controller configured to:
control the stiffness variable unit to change the bending stiffness of the insertion section to a first bending stiffness when the advance and retreat sensor has detected the advance of the insertion section, and control the stiffness variable unit to change the bending stiffness of the insertion section to a second bending stiffness higher than the first bending stiffness when the advance and retreat sensor has detected the retreat of the insertion section;
wherein the advance and retreat sensor comprises a shape detection portion that is incorporated into the insertion section and detects a shape of the insertion section; and
the controller is further configured to detect the advance of the insertion section or the retreat of the insertion section, based on a change in shape of the insertion section made in accordance with a push operation or a pull-back operation of the insertion section.

2. The flexible tube insertion apparatus according to claim 1, wherein
the controller detects a bent part of the insertion section based on the shape of the insertion section, and
the controller detects the advance of the insertion section when a radius of the bent part is decreased by the push operation, and detects the retreat of the insertion section when the radius of the bent part is increased by the pull-back operation.

3. The flexible tube insertion apparatus according to claim 2, wherein
the insertion section is divided into a plurality of segments arranged in a column shape along an axis direction,
the stiffness variable unit includes one or more stiffness variable actuators configured to vary the bending stiffness of the insertion section in units of the segments, and
the controller controls a stiffness of the stiffness variable actuators corresponding to the segment arranged in the bent part.

4. The flexible tube insertion apparatus according to claim 1, comprising:
a motor that drives the stiffness variable unit based on a control instruction from the controller, wherein the stiffness variable unit includes:
a coiled sheath member incorporated into the insertion section; and
a wire that is inserted through an inside of the sheath member and that contracts the sheath member by actuating the motor, and
the stiffness variable unit uniformly varies the bending stiffness of the entire insertion section.

* * * * *